United States Patent
Prabhakarpandian et al.

(10) Patent No.: US 8,940,494 B2
(45) Date of Patent: Jan. 27, 2015

(54) MICROFLUIDIC ASSAY IN IDEALIZED MICROVASCULAR NETWORK FOR CHARACTERIZATION OF LEUKOCYTE ADHESION CASCADE

(71) Applicant: CFD Research Corporation, Huntsville, AL (US)

(72) Inventors: Balabhaskar Prabhakarpandian, Madison, AL (US); Kapil Pant, Huntsville, AL (US)

(73) Assignee: CFD Research Corporation, Huntsville, AL (US)

( * ) Notice: Subject to any disclaimer, the term of this patent is extended or adjusted under 35 U.S.C. 154(b) by 0 days.

(21) Appl. No.: 13/743,171

(22) Filed: Jan. 16, 2013

(65) Prior Publication Data
US 2013/0149735 A1    Jun. 13, 2013

Related U.S. Application Data

(63) Continuation-in-part of application No. 13/715,350, filed on Dec. 14, 2012, which is a continuation-in-part of application No. 12/612,573, filed on Nov. 4, 2009, now Pat. No. 8,380,443.

(51) Int. Cl.
| | |
|---|---|
| *G01N 33/554* | (2006.01) |
| *C12Q 1/02* | (2006.01) |
| *G01N 33/50* | (2006.01) |
| *G01N 33/543* | (2006.01) |
| *G01N 33/569* | (2006.01) |

(52) U.S. Cl.
CPC ............ *C12Q 1/025* (2013.01); *G01N 33/5008* (2013.01); *G01N 33/54366* (2013.01); *G01N 33/5029* (2013.01); *G01N 33/5032* (2013.01); *G01N 33/5047* (2013.01); *G01N 33/56972* (2013.01)
USPC .......................................... 435/7.24; 435/176

(58) Field of Classification Search
None
See application file for complete search history.

(56) References Cited

U.S. PATENT DOCUMENTS

| | | | | |
|---|---|---|---|---|
| 6,900,021 | B1 * | 5/2005 | Harrison et al. | 435/7.21 |
| 7,790,443 | B2 * | 9/2010 | Wikswo et al. | 435/289.1 |

FOREIGN PATENT DOCUMENTS

WO    WO 2004020341 A2 *    3/2004

* cited by examiner

*Primary Examiner* — Jon P Weber
*Assistant Examiner* — Teresa E Knight
(74) *Attorney, Agent, or Firm* — Maschoff Brennan, PPLC

(57) ABSTRACT

Methods of assaying the leukocyte adhesion cascade (LAC) and monitoring leukocyte rolling, adhesion, and/or migration can be implemented with an apparatus that includes an idealized microvascular network (IMN) of one or more interconnected idealized flow channels in fluid communication through a porous wall with a tissue space (e.g., idealized tissue space). The methods of assaying the LAC can be implemented with means for quantifying modulation of the leukocyte adhesion cascade. Methods of assaying the LAC can be implemented with the device and one or more active agents to monitor leukocyte rolling, adhesion, and/or migration in the presence of absence of the active agent. Migration can be through the idealized flow channels, through the porous wall, and/or into the tissue space.

28 Claims, 19 Drawing Sheets

Symmetric Diameter, Symmetric Angle

Asymmetric Diameter, Symmetric Angle

Asymmetric Diameter, Asymmetric Angle $d_1/d_2 \neq 1$ $\theta_1/\theta_2 \neq 1$ Serial and Parallel Arrangement of Bifurcations and Junctions Serial and Parallel Arrangement of Bifurcations and Junctions Serial and Parallel Arrangement of Bifurcations and Junctions

MICROFLUIDIC ASSAY IN IDEALIZED MICROVASCULAR NETWORK FOR CHARACTERIZATION OF LEUKOCYTE ADHESION CASCADE

CROSS-REFERENCE TO RELATED APPLICATIONS

This patent application is a continuation-in-part of U.S. Ser. No. 13/715,350 filed Dec. 14, 2012, which is a continuation-in-part of U.S. Ser. No. 12/612,573 filed Nov. 4, 2009 now U.S. Pat. No. 8,380,443; which patent applications are incorporated herein by specific reference in their entirety.

STATEMENT REGARDING GOVERNMENT SPONSORED RESEARCH

Not Applicable.

BACKGROUND

The leukocyte adhesion cascade, a multistep process mediated by a series of receptor-ligand interactions, is important to many physiological and pathophysiological processes of the body. A number of in vitro models have been developed to study different aspects of the leukocyte adhesion cascade and to develop and test anti-inflammatory agents and other drugs. Flow chambers have been developed to study rolling and adhesion phenomena, and Boyden and transwell chambers have been used for migration studies.

Flow chambers provide physiological shear but cannot model transmigration. Transwell and Boyden chambers do not account for fluid shear and size/topology observed in vivo or provide real-time visualization of leukocyte migration, measure leukocyte migration semi-quantitatively, and are labor intensive. No experimental model currently resolves rolling, adhesion and migration in a single in vitro assay. As a consequence, understanding of the leukocyte adhesion cascade and anti-inflammation drug development has been limited. For example, a leukocyte migration inhibitor in Boyden chambers may fail to work in realistic flow shear. The method and apparatus of the present invention provide a rapid assay for anti-inflammatory markers and drugs targeted to affect the leukocyte adhesion cascade.

SUMMARY

In one embodiment, a method for identifying one or more agents that modulate leukocyte rolling, adhesion, and/or migration can be performed. The method can be performed with an optically transparent microfluidic chip comprising one or more idealized flow channels having one or more inlets and one or more outlets and a first cross-sectional dimension, and one or more tissue spaces bordering and fluidly coupled with the one or more idealized flow channels and having a second cross-sectional dimension, wherein a first wall separating a first idealized flow channel from a first tissue space includes a plurality of apertures that fluidly couple the first idealized flow channel with the first tissue space, the plurality of apertures having a third cross-sectional dimension. The method can be performed by flowing a suspension of leukocytes through the one or more idealized flow channels, flowing a solution containing one or more agents through the one or more idealized flow channels before, during, or after flowing the suspension of leukocytes, and locating and counting leukocytes in the microfluidic chip. Based upon the locations and numbers of leukocytes, determining whether the one or more agents modulate leukocyte rolling, adhesion, and/or migration. In one aspect, the third cross-sectional dimension is smaller than the first cross-sectional dimension and the second cross-sectional dimension is larger than the first cross sectional dimension. In another aspect, the first cross-sectional dimension is from 10 microns to 500 microns, the second cross-sectional dimension is from about 100 microns to 1 cm, and the third cross-sectional dimension is from 0.2 micron to 30 microns.

In one embodiment, the one or more idealized flow channels form an idealized microvascular network having a plurality of idealized flow channels. In one aspect, the idealized microvascular network includes one or more idealized flow channels interconnected by one or more idealized bends, junctions, or bifurcations. In one aspect, the one or more idealized bends, junctions or bifurcations include one or more acute, right, or obtuse angles. In one aspect, luminal surfaces of the one or more idealized flow channels of the idealized microvascular network are coated with a first cell type and the one or more tissue spaces are either devoid of cells or include a different second type of cell. In one aspect, the apertures and/or one or more tissue spaces are filled with a material that is permeable to the leukocytes, wherein the material is selected from a gel, a basement matrix, an extracellular matrix, a tissue matrix, a synthetic matrix, a natural matrix, polymer, hydrogels, and combinations thereof.

In one embodiment, the angles of the one or more idealized bends, junctions, or bifurcations range from 15° to 135°. In one aspect, a first bifurcation having a first idealized daughter flow channel with a cross-sectional dimension that is greater than a cross-sectional dimension of a second idealized daughter flow channel of the first bifurcation. In one aspect, a first bifurcation having a first idealized daughter flow channel at an angle that is greater than an angle of a second idealized daughter flow channel of the first bifurcation.

In one aspect, a first bifurcation having a first idealized daughter flow channel with a cross-sectional dimension that is greater than a cross-sectional dimension of a second idealized daughter flow channel of the first bifurcation and a first idealized daughter flow channel being at an angle that is greater than an angle of a second idealized daughter flow channel.

In one embodiment, the first type of cell includes endothelial cells, and the second type of cell includes healthy or diseased endothelial cells, epithelial cells, fibroblasts, bone marrow cells, embryonic cells, hepatocytes, myocytes, neural cells, adipocytes, brain cells, liver cells, heart cells, kidney cells, lung cells, stomach cells, intestine cells, pancreas cells, ovary cells, cervix cells, spleen cells, artery cells, venule cells, capillary cells, connective tissue cells, organ tissue boundary layer cells, connective tissue cells, muscle cells, bone cells, nervous tissue cells, germ cells, stem cells, leukocytes, erythrocytes, platelets, healthy and diseased cells, cultures thereof, 3D tissues thereof, and combinations thereof.

Tumor cells, as used herein, includes primary and cultured neoplastic cells derived from naturally occurring or artificially induced tumors, as well as normal cells transformed with exogenous nucleic acid to produce neoplastic cell lines. The tumor cells can be immortalized or primary cells. The tumor cells can be obtained from a patient that has cancer, and cultured in the tissue space of the device described herein.

In one embodiment, the one or more tissue spaces are defined by at least two of the idealized flow channels having walls that each include the plurality of apertures that fluidly couple the at least two straight flow channels with the first tissue space. In one aspect, the at least two idealized flow channels each include idealized flow channels connected at idealized bends, junctions, or bifurcations to form at least two distinct flow channel lumen that define the first tissue space. In one aspect, each wall separating one or more idealized flow channels from the first tissue space include the plurality of apertures that fluidly couple the at least two straight flow channels with the first tissue space.

In one embodiment, location and counting of leukocytes is performed by optical means. In one aspect, the optical means includes a camera in communication with an automated stage upon which the microfluidic chip is mounted.

In one embodiment, the one or more agents that modulate leukocyte rolling, adhesion or migration is selected from the group consisting of cells, liposomes, lipisomes, lipoproteins, microencapsulated drugs, particulate drug carriers, nanoparticles, microparticles, polymer beads, naturally occurring proteins, synthetic proteins, natural compounds, synthetic compounds, and combinations thereof.

In one embodiment, the step of flowing the one or more agents is performed using a flow scheme selected from a single pass, a multiple pass, a recirculating circulation loop, and combinations thereof.

In one embodiment, the method can include measuring a property of the one or more agents, said property selected from the group consisting of real time circulation, stability, half-life, aggregation, degradation, and combinations thereof.

In one embodiment, the step of flowing the solution containing the agent is performed using varying fluidic shear rate values of between 1 $sec^{-1}$ and 2000 $sec^{-1}$ or up to 5000 $sec^{-1}$.

In one embodiment, the solution containing the one or more agents includes a component selected from the group consisting of serum proteins, whole blood, apheresed blood, eukaryotic cells, bacteria, erythrocytes, platelets, viruses, and combinations thereof.

In one embodiment, the one or more tissue spaces contain one or more substances selected from the group consisting of an extracellular matrix, a basement membrane, a synthetic matrix, natural occurring matrix, a cytokine, a cell that secrete a cytokine, a gel, a cell culture, a source of a leukocyte chemo-attractant, and combinations thereof.

In one embodiment, the method includes determining a correlation between flow rate and shear rate for the microfluidic chip and using the determined correlation to set a flow rate for the step of flowing the suspension of leukocytes.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1:
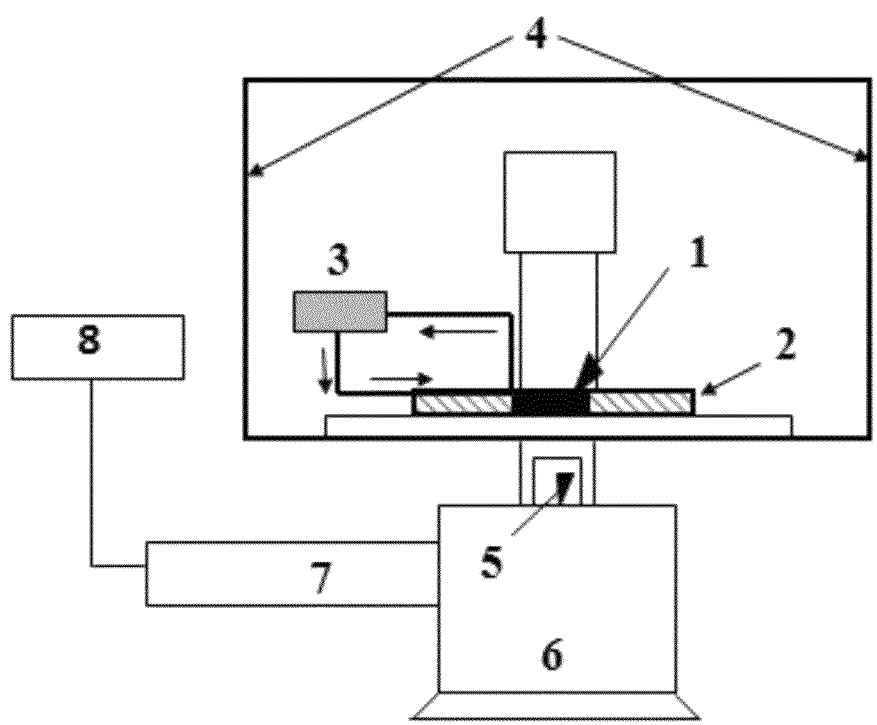
FIG. 1 is a drawing showing the components of a system used for leukocyte adhesion cascade assays.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The present invention relates to an in vitro assay for characterization of the leukocyte adhesion cascade. More specifically, the invention relates to a leukocyte adhesion and migration assay using a microfluidic apparatus.

The apparatus and method described herein address a need in the art for an assay capable of identifying and screening for agents affecting the leukocyte adhesion cascade (LAC) encompassing rolling, adhesion, and migration. The LAC assay device comprises an optically clear, plastic microfluidic chip comprising flow channels with diameters in the range of 10-500 μm. The luminal walls of the flow channels can be coated with endothelial cells and the walls of at least a portion of the flow channels may contain 0.2-30 μm sized openings, pores, or gaps, optionally filled with a native or synthetic extracellular matrix, that allow leukocyte migration into one or more tissue spaces. The flow channels may be linear or bifurcating channels, may form an idealized microvascular network (IMN), or they may be present in the form of a synthetic microvascular network (SMN). In contrast with current in-vitro models, this device resolves and facilitates direct assessment of individual steps in the leukocyte adhesion cascade including rolling, firm arrest (adhesion), spreading, and extravasation of the leukocytes into the extra-vascular tissue space. The present assay may include quantitative end point measurement, real-time visualization of cell migration, and automation of assay method steps.

A "microfluidic chip" is constructed using well known techniques employed in the semiconductor industry such as photolithography, wet chemical etching, thin film deposition and soft lithography using polymeric substrates, such as Polydimethylsiloxane (PDMS). This is in contrast to microfluidic systems formed in gels made of proteins, chitosan, proteoglycans, and/or other extracellular matrix components. In general, a microfluidic chip is formed with a number of microchannels that are connected to a variety of reservoirs containing fluid materials. The fluid materials are driven or displaced within these microchannels throughout the chip using electrokinetic forces, pumps and/or other driving mechanisms.

A "synthetic microvascular network" (SMN) is a manmade network comprising interconnected, nonlinear flow channels that form geometrical features and have fluid flow properties found in physiological microvascular networks. The flow channels (synthetic vessels) form intersecting networks and may be arranged end to end, analogous to an arteriole, capillary, venuole sequence. Flow channels and the SMNs they form possess geometric characteristics of physiological microvascular including variable cross-sectional shapes, variable cross-sectional areas, convolutions, turns, and/or anastomoses. A network of linear channels joining at angles, for example, is not an SMN because such a network possesses geometrical shapes and produced flow characteristics not found in physiological microvascular networks. Straight channels or other channels having non-physiological geometries may be used to link a synthetic microvascular network to other components of a microfluidic chip. These channels, however, are not a part of the microvascular network. One or more flow channels of a SMN may comprise porous walls such that liquid may move from the interior (lumen) of the flow channel into a space external to the lumen in a manner similar to the movement of fluid from the lumen of a physiological vessel into an interstitial space.

An idealized microvascular network (IMN) is a manmade network comprising interconnected flow channels that have certain fluid flow properties found in physiological microvascular networks. The diameters of the channels range from 10-500 μm and comprise of angles typically between 15° and 135°. One or more flow channels of an IMN may comprise porous walls such that liquid may move from the interior (lumen) of the flow channel into a space external to the lumen in a manner similar to the movement of fluid from the lumen of a physiological vessel into an interstitial space. The pores can be considered to be gaps or apertures that fluidly couple the flow channel and tissue space.

As used herein, the term "idealized" in association with a microfluidic network, junction, or bifurcation is used to describe a synthetic network, junction, or bifurcation consisting of straight microfluidic channels joined at acute, right, or obtuse angles.

As used herein, the word "bifurcation" is meant to include a parent channel splitting into two or more daughter channels. The channels comprising a bifurcation have walls made of a manufactured substrate and may be coated with biological molecules and/or cells. It is further understood that in a general context, a "bifurcation" may also be a junction, which has the same structure as a bifurcation but in which fluid flows in the opposite direction from the daughter channels into the parent channel.

As used herein, a microfluidic channel may have a rectangular, circular, semi-circular, irregular or a combination of cross-sectional shapes. The dimensions of a channel are described, for example, by length, depth and width wherein the depth is measured perpendicular to the plane of a microfluidic chip containing the channel and length and width are measured in directions lying in the plane of the microfluidic chip containing the channel. Channels having circular or semi-circular cross-sections may be described as having variable depth and width relative to channels having rectangular cross-sections or may alternatively be described in terms of channel diameter. Maximum depth and width when used to describe a channel having a circular or semi-circular cross-section are both equal to the maximum diameter of the channel. When used to describe a channel having a rectangular cross-section, the maximum width and depth refer to the constant width and depth of a channel having a constant width and depth or to the highest values for width and depth for channels having variable width and depth.

A microfluidic chip is constructed using techniques employed in the semiconductor industry such as photolithography, wet chemical etching, thin film deposition and soft lithography using polymeric substrates, such as Polydimethylsiloxane (PDMS). Other materials that may be used in place of PDMS include Poly(Styrene Butadiene Styrene) (SBS) and Poly(Styrene-Ethylene-Butadiene-Styrene) (SEBS) elastomers, Polyester-ether (PEE) thermoplast, and thermoset polyester (TPE), which can be used for replica molding fabrication techniques. Polyolefin plastomer (POP's) can be specifically used for submicron range channels. Glass or quartz with reactive wet/dry etching of the microchannels can also be used. Thermoplastic materials such as polymethylmethacrylate (PMMA), polycarbonate (PC), cyclic olefin copolymer (COC), polystyrene (PS), poly vinyl chloride (PVC), and polyethylene terephthalate glycol (PETG) can be used with embossing techniques or injection molding. PS, PC, cellulose acetate, polyethylene terephthalate (PET), PMMA, PETG, PVC, PC, and polyimide can also be used with laser ablation techniques. In general, a microfluidic chip is formed with a number of microchannels that are connected to a variety of reservoirs containing fluid materials. The fluid materials are driven or displaced within these microchannels throughout the chip using electrokinetic forces, pumps and/or other driving mechanisms.

"Tortuosity" is a measure of the indirectness of a vessel or flow channel path. Tortuosity can be measured in several ways. One exemplary means of measuring tortuosity is to sum the angles between consecutive trios of points along the space curve represented by a vessel skeleton and then normalize by path length. Tortuosity may also be measured, for example, by counting inflection points along each vessel or flow channel and multiplying this number (plus one) times the total path length and then dividing by the distance between the ends of the each vessel or flow path.

Assay System:

FIG. 1 shows a non-limiting example of a system for performing leukocyte adhesion cascade assays according to the present invention. The system comprises a pumping means (3) such as a peristaltic pump (for recirculation/multiple pass) or a syringe pump (single pass) to move fluids through microfluidic channel networks. For experiments with a peristaltic pump, a microfluidic chip (1) is placed on an automated stage device (2) and connected to a pump (3) that is connected to inlets, outlets, and, optionally, ports on the microfluidic chip (1). The microfluidic chip (1) is preferably contained within an incubation chamber (4) and is positioned over an objective lens (5) of a brightfield, phase contrast or fluorescent microscope (6). Optical means such as a CCD/CMOS camera or video camera (7) are used to visualize cells within the microfluidic chip (1). The camera (7) is in communication with a computer (8) for data collection and control of microscope (6), camera (7), and the microscope mounted accessories. For experiments with a syringe pump, the syringe pump (3) is connected to the microfluidic chip (1) and fluid leaving the microfluidic chip (1) is sent to a waste reservoir (not shown). Also, fluid may be recirculated through the microfluidic chip (1) as shown in the figure or may be pumped in a single pass mode from the pump (3) to a waste reservoir (not shown).

Figure 2A:
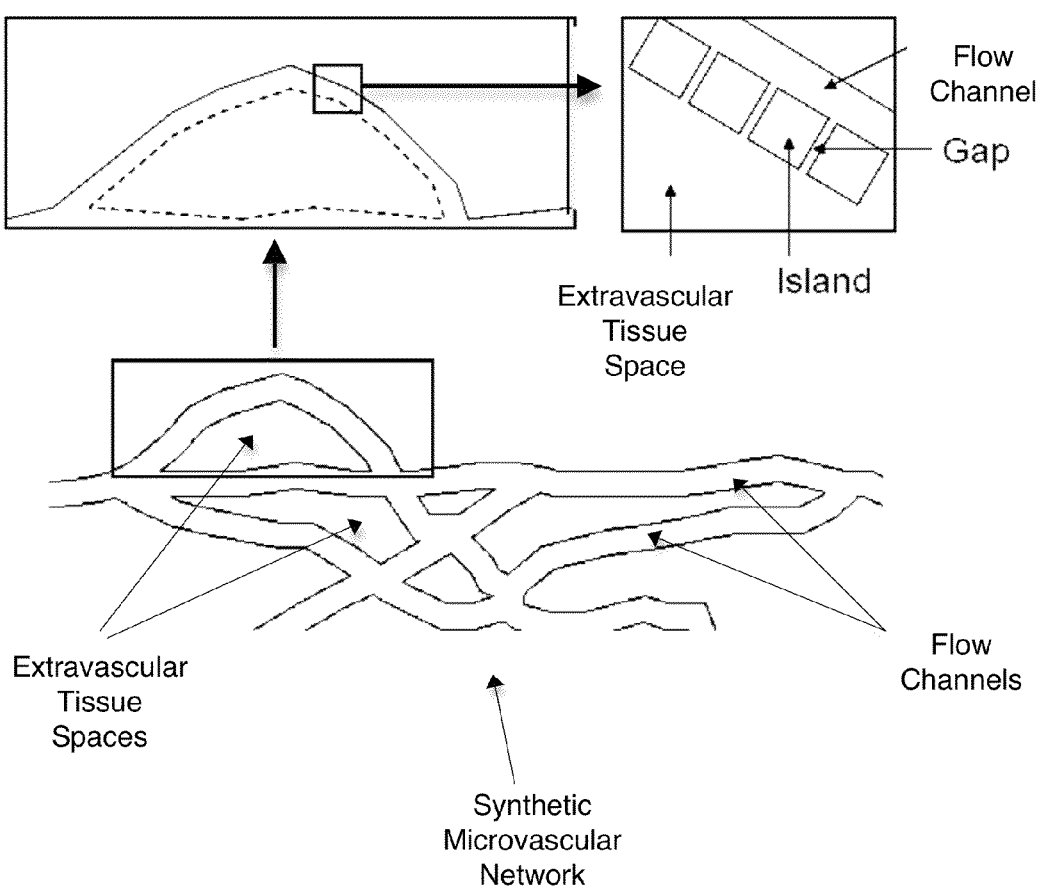
FIGS. 2A-2C include drawings showing embodiments of SMN on a microfluidic chip.

Microfluidic Chips:

The microfluidic chips used in the assay system may comprise one or more SMNs, one or more IMNs, or a combination of SMNs and IMNs. FIG. 2A shows several views of a SMN in a microfluidic chip according to the invention. The SMN is made of interconnected nonlinear flow channels that form a geometry that provides physiological flow conditions including convective flow and diffusion. The geometry of the SMN is derived from one or more images of one or more in vivo microvascular networks. The SMN comprises extravascular tissue spaces separated from the lumen of flow channels by porous walls that allow liquid to diffuse from the flow channels into the tissue spaces. The tissue spaces preferably have cross-sectional luminal dimensions of between 100 μm and 1 cm. In this example, the walls of flow channels surrounding the tissue spaces are constructed with 0.2-30 μm wide gaps to allow liquid diffusion. The portions of the walls of the flow channels between gaps are referred to as islands.

The tissue spaces in a SMN or an IMN preferably comprise a port that serves as an inlet and an outlet for introducing fluid and cells into the tissue spaces and for removing liquid and cells from the tissue spaces. Tissue spaces may also have separate inlets and outlets. The pressure inside each tissue space is preferably regulated through an inlet/outlet port or through a dedicated pressure valve. The walls of at least some of the flow channels that also form the walls of a tissue space are porous to liquids such as aqueous buffers to allow diffusion from the lumen of the microvascular network into the lumen of the tissue space. Porosity may be achieved, for example, by way of gaps, perforations, and/or pores present in the walls of the flow channels. The walls of the flow channels may preferably be coated with a confluent layer of primary or cultured endothelial cells. This may be facilitated by first coating the walls of the flow channels with basement matrix such as Matrigel™, collagen, or other extracellular matrix (ECM) components.

Figure 2B:
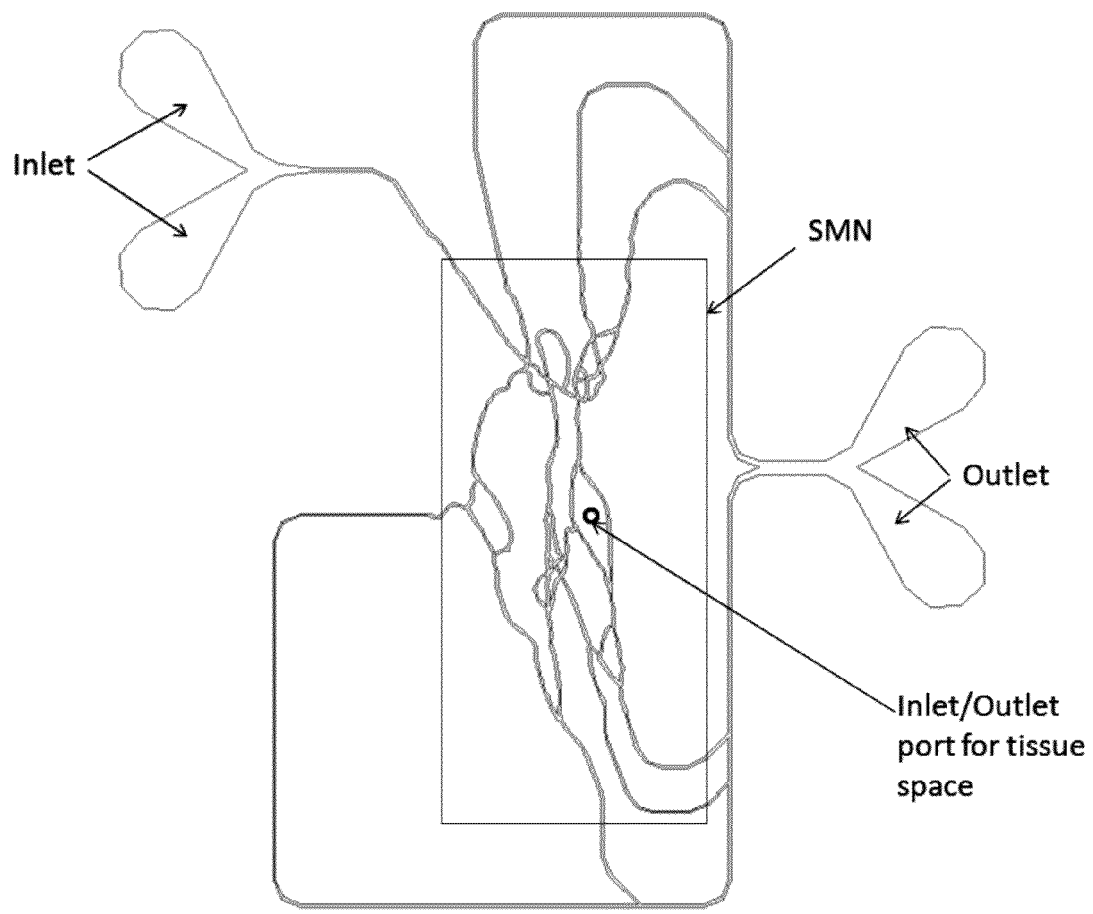
Figure 2C:
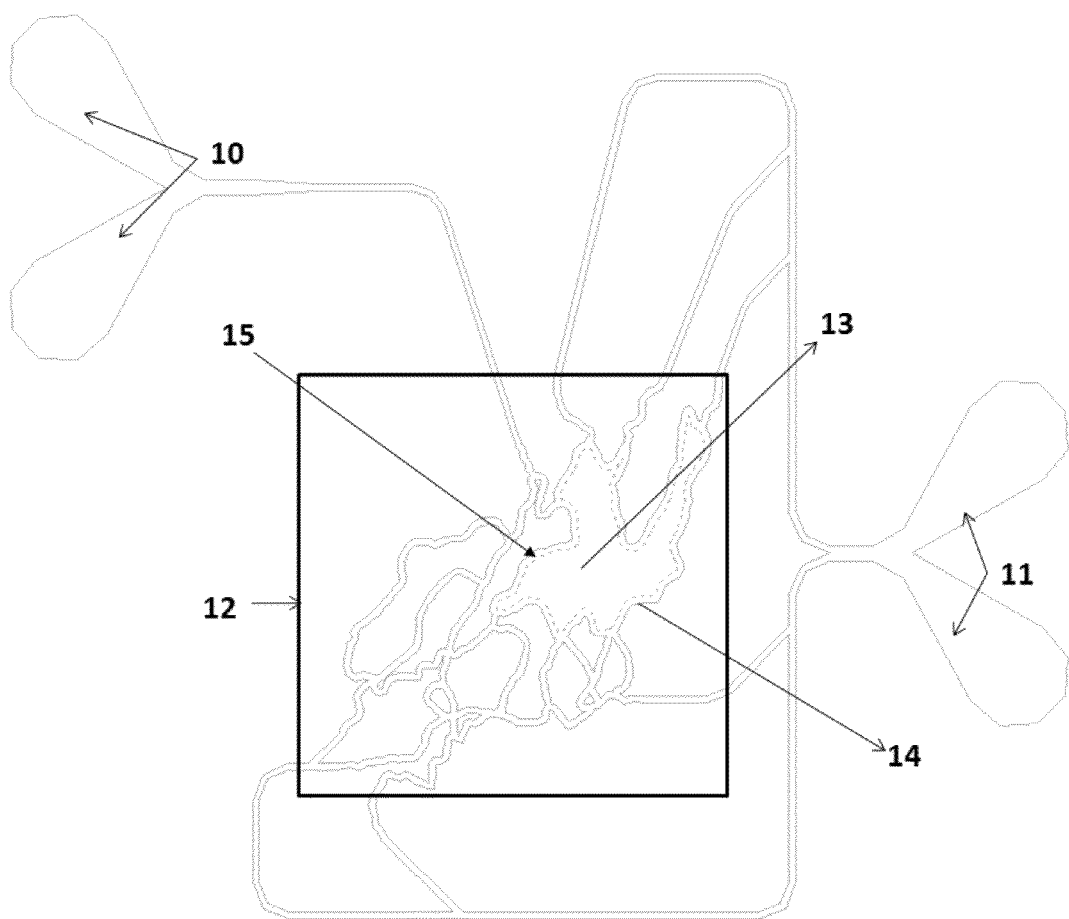

FIG. 2B shows an example of a microfluidic chip comprising a SMN. The SMN comprises one or more tissue spaces containing a port that serves as an inlet into and an outlet from the tissue space. The SMN is in fluid communication with an inlet and an outlet via microfluidic channels connected to nonlinear flow channels in the SMN. FIG. 2C shows a SMN (12) that comprises a plurality of interconnected, nonlinear flow channels (14), in fluid communication with one or more inlets (10) and one or more outlets (11). One or more extravascular/tissue spaces (13) are separated from and in fluid contact with flow channels of the SMN via gaps or pores (15) having dimensions of between 0.2 and 30 micrometers in the wall of at least one flow channel (14) adjacent to at least one tissue space (13). The cross-section may be a diameter in the case of circular pores or may be the length of the longest side for rectangular gaps.

Obtaining Geometries for SMNs:

The geometries for SMNs are derived from physiological microvascular networks. A geometry may, for example, be an exact replica of a digitized image of a natural microvascular network or an average of several digitized images. Maps of complete microvascular networks are constructed from a collage of arterioles, capillaries and venuoles. An entire network is digitized by tracing each vessel on the assembled collage in AutoCad Map™ using a computerized drawing board such as Drawing Board III™, CalComp.

After a network is digitized, an AutoCad Map™ cleanup routine is used to ensure all vessels are properly connected at their common nodes. A tolerance value is set which distinguishes between common nodes and neighboring end points. Each vessel is graphically represented by a polyline consisting of a series of straight lines connected through vertices. The system compares the distances between successive vertices in a polyline to the set tolerance value. The vertex is removed from the polyline if the distance is below the set tolerance value. Images of physiological microvascular networks for use in obtaining geometries may also be obtained using digital photography (e.g. retinal imaging).

Reconstructed "Averaged" Microvascular Networks:

Averaged or nominal microvascular networks are based on the geometries of at least two actual physiological microvascular networks. The images are analyzed as described above and subjected to a detailed morphological analysis to yield statistical data of morphometric parameters such as ratios of parent to daughter vessel diameters, branching angles, distances between branches, rations of branch length to branch channel diameter, tortuosity, bifurcation branch density, and recombining branch density. Averaged microvascular networks can be generated by using averaged morphometric data and/or stochastic sampling of probability density functions for morphometric data. Averaged microvascular networks may be generated using values selected from a variety of statistical distributions for individual morphometric parameters. The values used need not be "average," "mean," or "median" values for measured morphometric parameters.

Idealized Microvascular Networks (IMNs):

An idealized microvascular network (IMN) is a manmade network comprising a straight flow channel or two or more interconnected flow channels that have certain fluid flow properties found in physiological microvascular networks.

Figure 3:
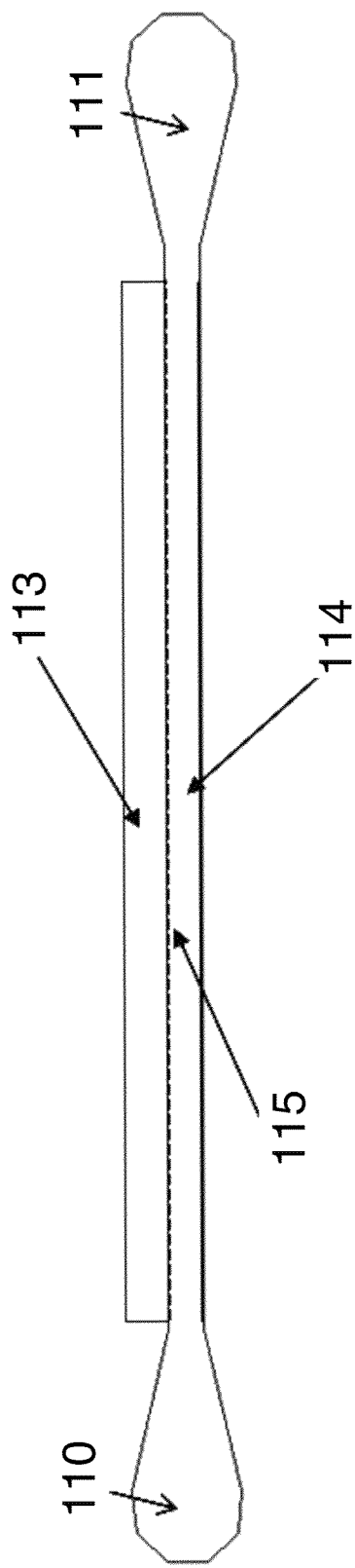
FIG. 3 is a drawing showing a single straight channel IMN with a tissue space separated by a porous wall.

FIG. 3 shows the boundary between a straight flow channel (114) and a tissue space (113) in an IMN embodiment of a microfluidic chip. Flow channel (114) is in fluid communication with inlet (110) and outlet (111) and borders tissue space (113) along an area of 0.2-30 μm gaps (115) with tissue space. Flow channel (114) may be a single, straight channel as shown or may be a portion of a bifurcated channel, in which case fluid communication with inlet (110) and outlet (111) may not be direct, as shown, but may be through additional flow channels.

Figure 4:
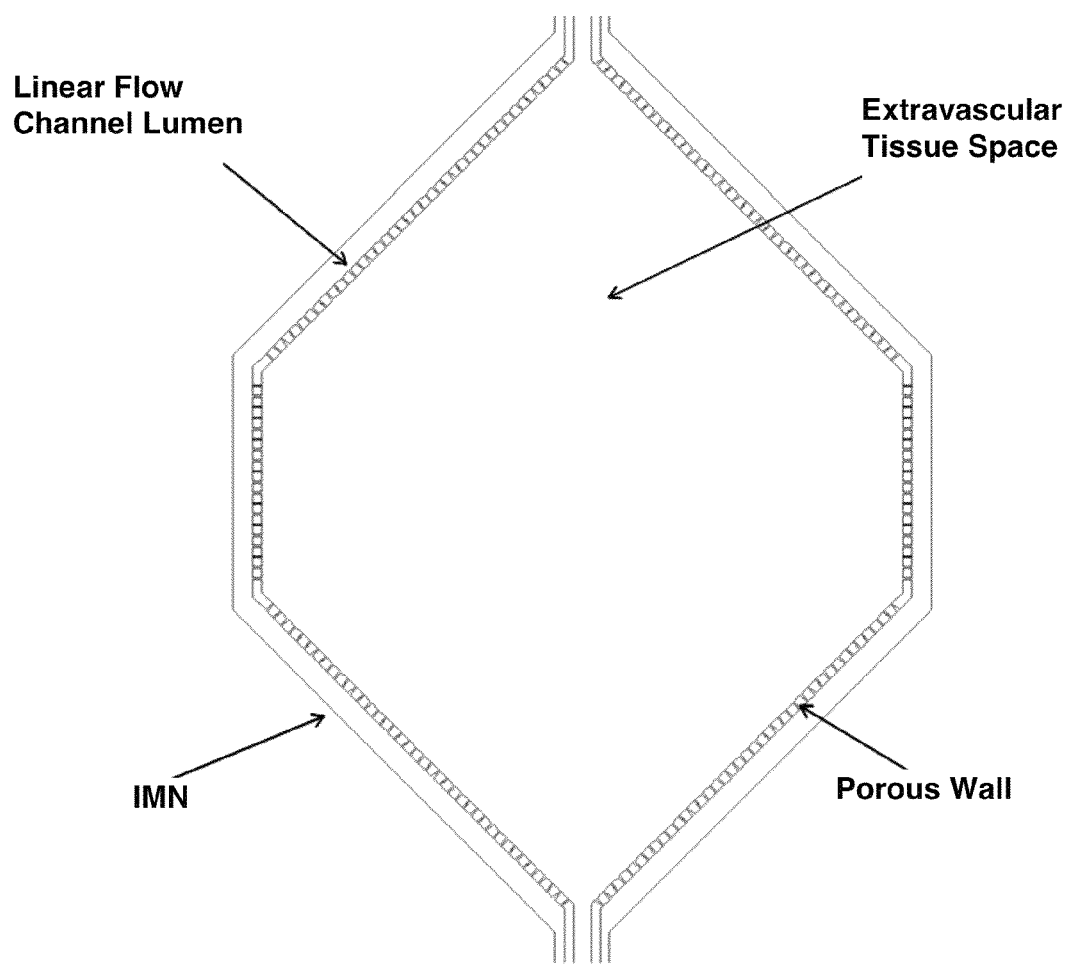
FIG. 4 is a drawing showing an IMN with a tissue space separated by a porous wall on a microfluidic chip.

FIG. 4 shows a portion of an IMN in a microfluidic chip. In this example, an extravascular tissue space is surrounded by linear flow channels. The walls of the linear flow channels contain gaps, preferably from 0.2 µm to 30 µm wide, or pores, preferably from 0.2 µm to 30 µm in diameter, that allow fluid to diffuse from the flow channels into the tissue space.

Figure 5:
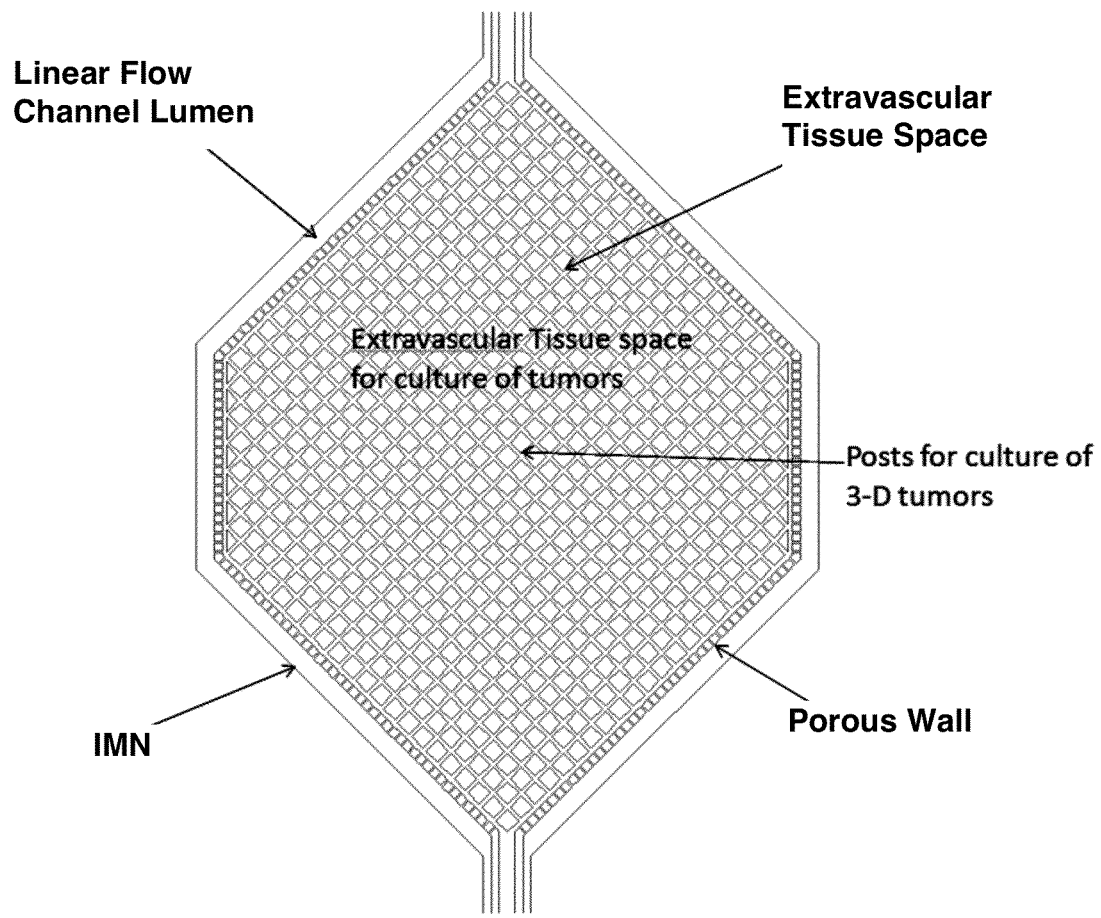
FIG. 5 is a drawing showing an IMN with a tissue space separated by a porous wall on a microfluidic chip for growing cells to simulate 3-dimensional tissues.

FIG. 5 shows a portion of an IMN comprising an extravascular tissue space that contains posts configured to facilitate the growth of adhesion dependent cells (e.g., tumor cells) to for a 3-dimensional tissue (e.g., solid tumor). While the network in this example is an IMN, 3-dimensional tissues may be grown in SMNs as well. Although the microfluidic chips and microvascular networks of the invention are largely planar, the depth of tissue spaces and the inclusion and arrangement of posts or other scaffolds within the tissue spaces can be designed to produce cell monolayers and bilayers, as well as 3-dimensional tissues. The location of each tissue space in the network may be selected by the user.

Figure 6:
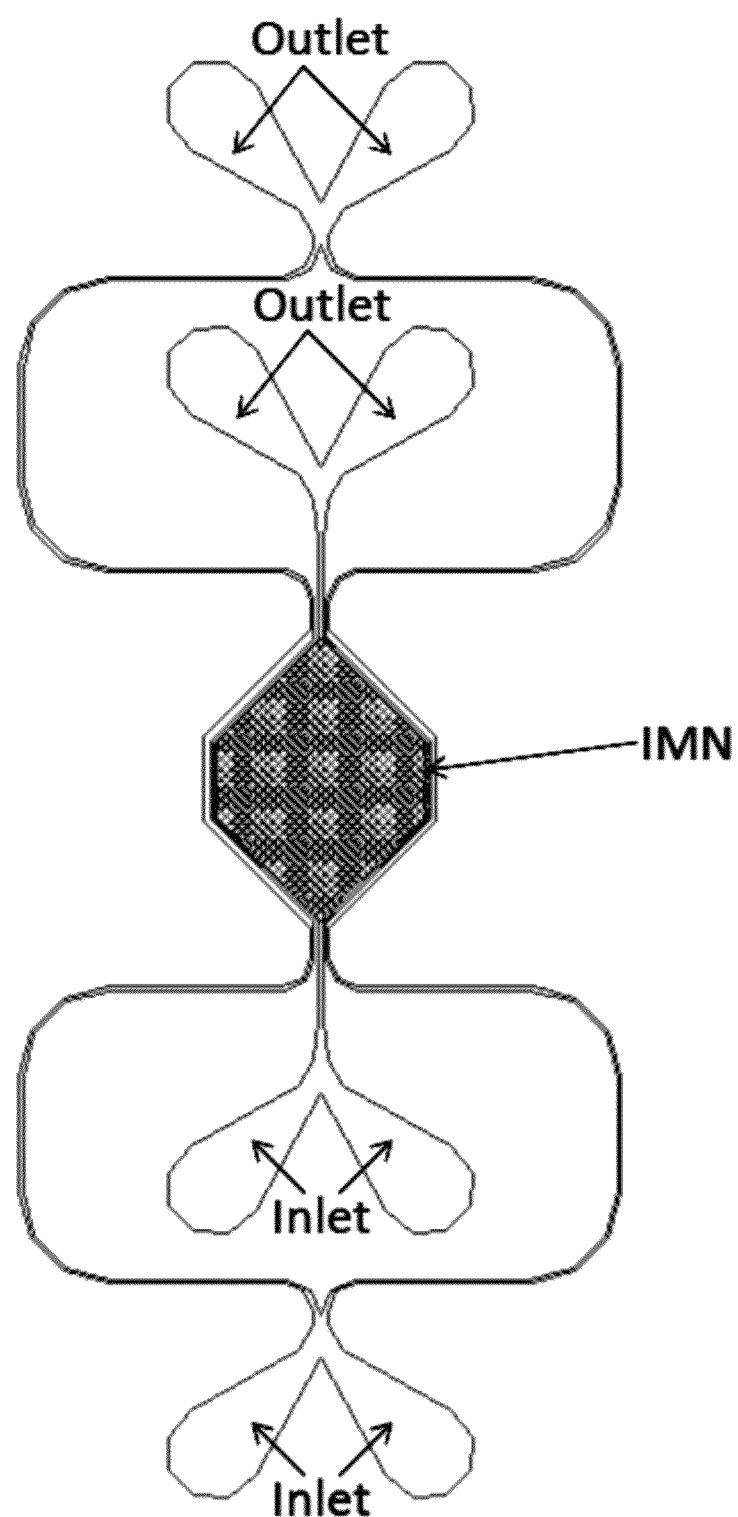
FIG. 6 is a drawing showing the components of a microfluidic chip used for leukocyte adhesion cascade assays using an IMN.
Figure 7:
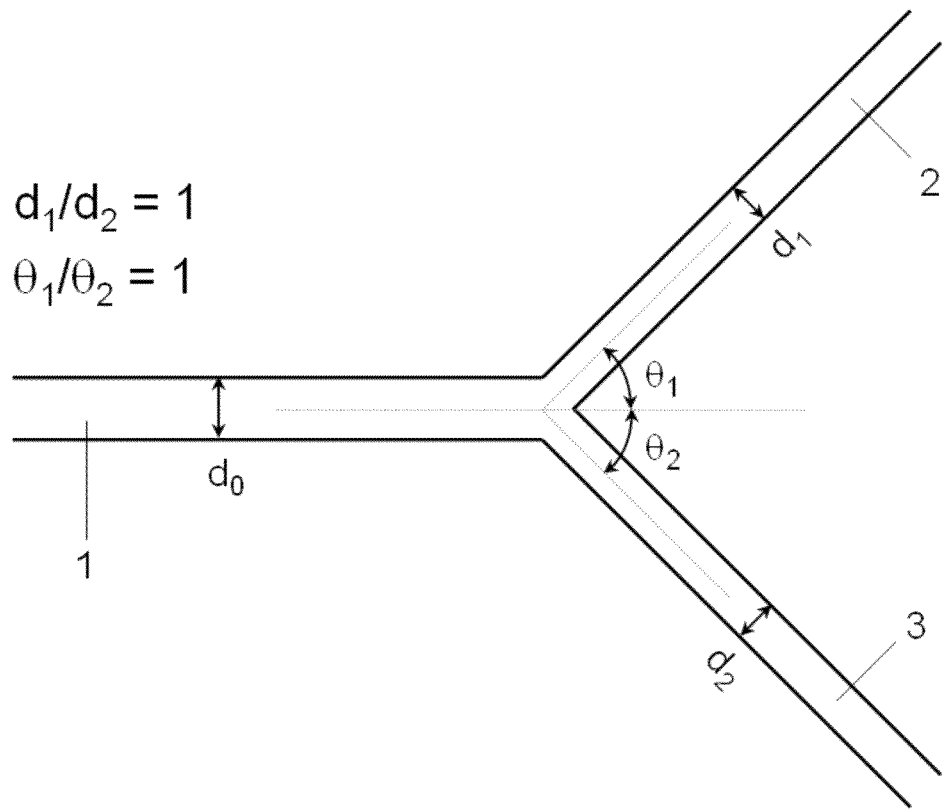
FIG. 7 shows a symmetric bifurcation with symmetric daughter diameters.
Figure 8:
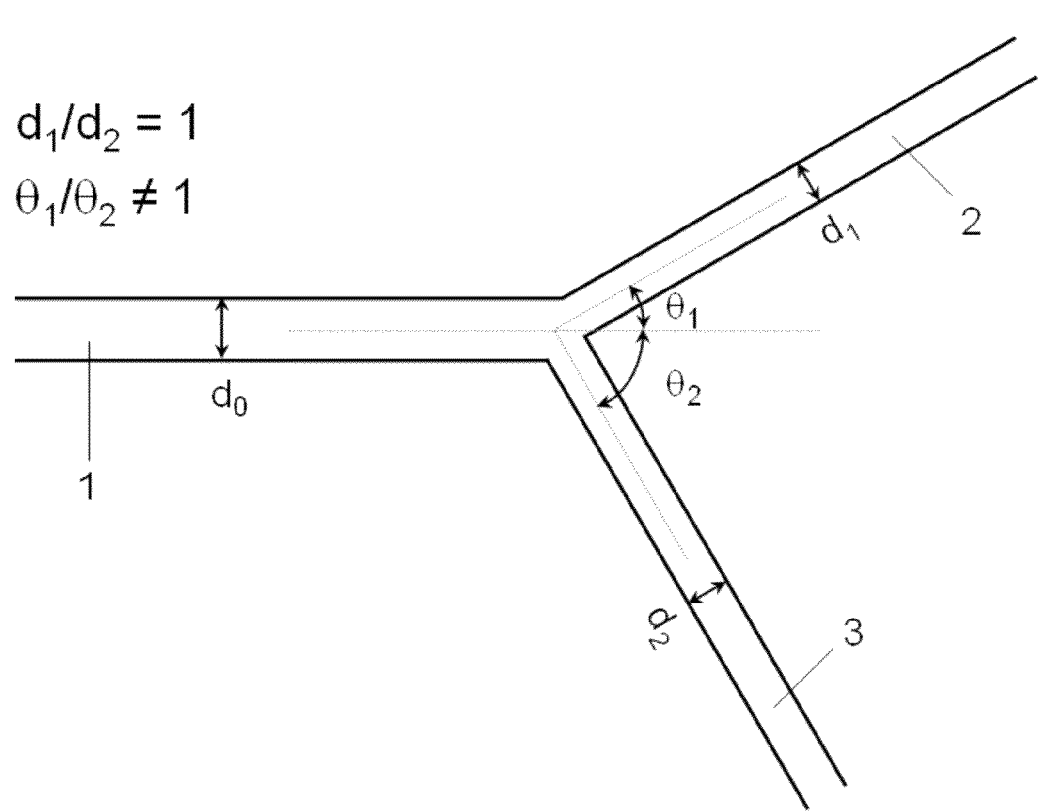
FIG. 8 shows an asymmetric bifurcation with symmetric daughter diameters.
Figure 9:
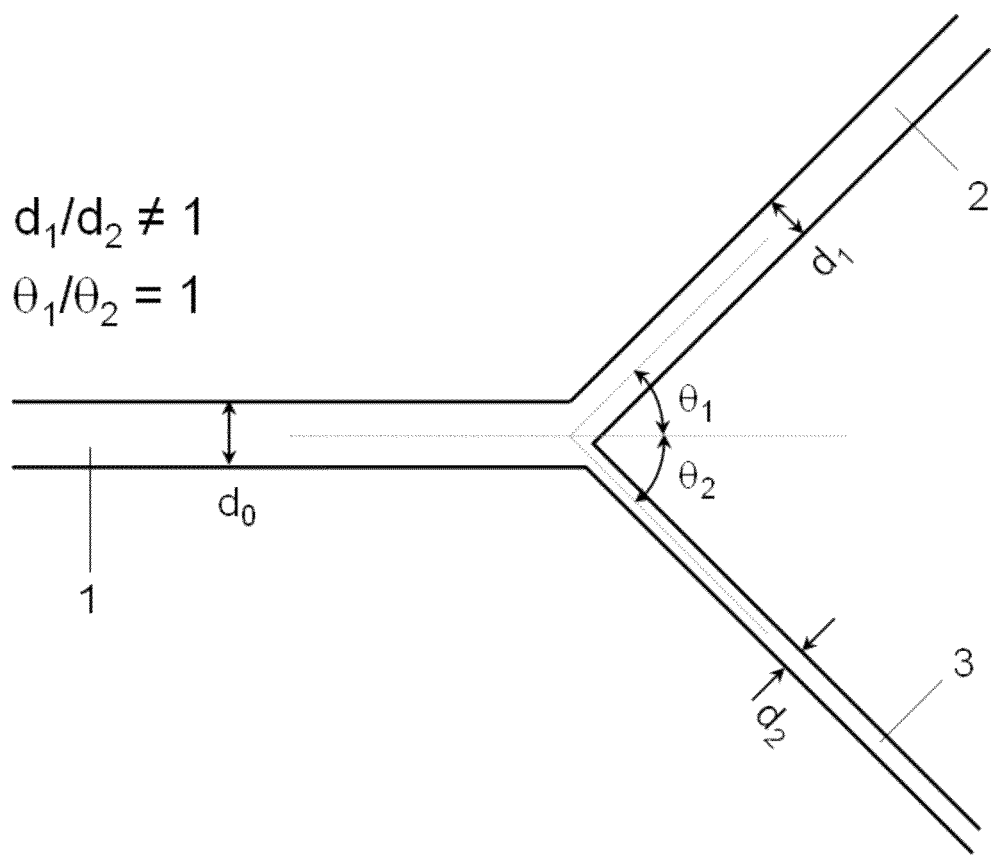
FIG. 9 shows a symmetric bifurcation with asymmetric daughter diameters.
Figure 10:
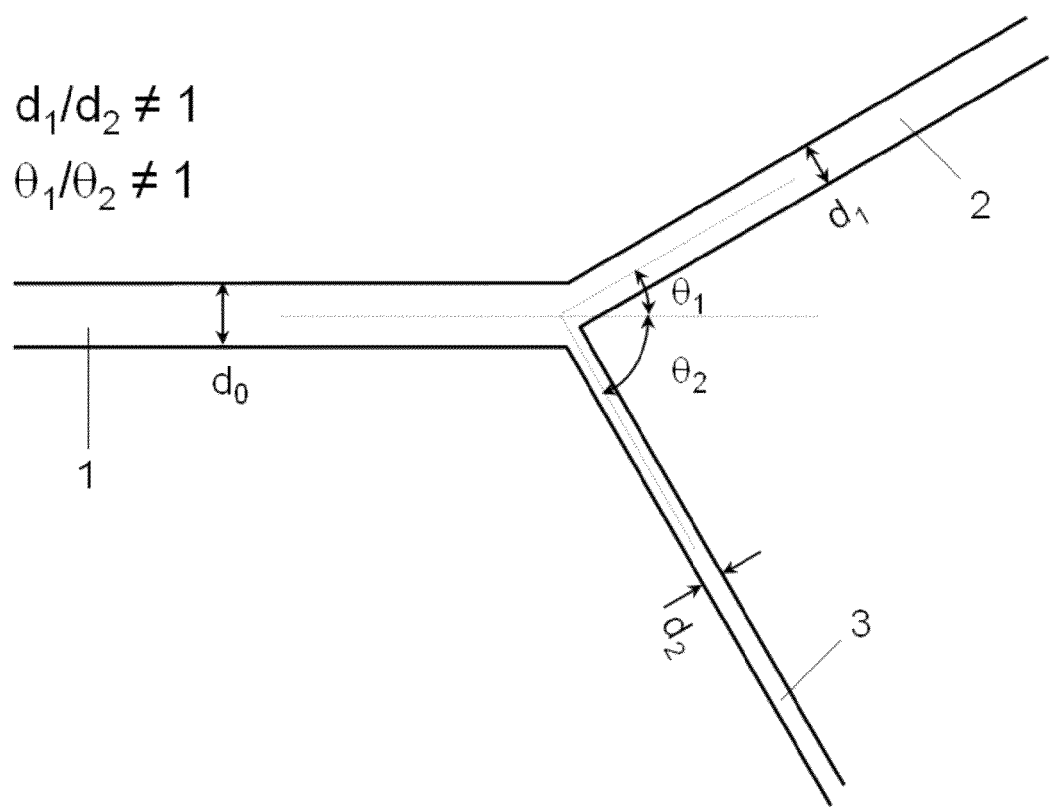
FIG. 10 shows an asymmetric bifurcation with asymmetric daughter diameters.

FIG. 6 shows an example of a microfluidic chip comprising an IMN, with a tissue space containing posts that serves as anchors to facilitate the formation of a 3-dimensional tissue (e.g., tumor). The posts can include a cross-sectional profile of any shape and appropriate dimension. For example, the posts can be circular, triangular, square, rectangle, pentagon, hexagon, polygon, irregular, or combinations thereof. The posts can have a cross-sectional profile with a dimension from one side to another that ranges from about 5 microns to about 100 microns, or from about 25 microns to about 75 microns, or preferably about 50 microns. The spacing between each posts can also be the same as mentioned above. The IMN and the tissue space are each in fluid communication with a fluid inlet and a fluid outlet. Separate dedicated inlets and outlets for the IMN and the tissue space allow fluid to be pumped through both the IMN and the tissue space. Fluid flows through the inlet and outlet of the IMN can be controlled to maintain specified flow rates and shear rates, for example. Fluid flow and/or pressure applied through the inlet and outlet of the tissue space may be controlled to maintain a simulated interstitial pressure or to simulate lymphatic drainage.

Idealized microvascular networks comprise single straight channels or multiple straight channels, and can include single or multiple bifurcations and/or junctions consisting of linear parent and daughter channels having rectangular or circular or semi-circular cross-sections that diverge or converge at angles of between 15° and 135°. The diameters or cross-sections of the channels are between 10 µm and 500 µm. The bifurcations and junctions are categorized as illustrated in FIG. 7 through FIG. 10. In the figures, $d_0$, $d_1$, and $d_2$ represent the diameters of the parent (1) and first and second daughter channels (2, 3), respectively. $\Theta_1$ and $\Theta_2$ represent the angles formed between the parent channel (1) and the first and second daughter channels (2, 3), respectively. "Diameter" in the context of channels having a rectangular cross-section refers to the longest cross-sectional distance and cross-sectional area is calculated as width×depth. For channels having circular cross-sections, cross-sectional area is calculated as diameter×diameter×π/4. For channels having semi-circular cross-sections, "diameter" refers to the longest cross-sectional dimension and cross-sectional area is calculated as diameter×diameter×π/8.

Figure 11:
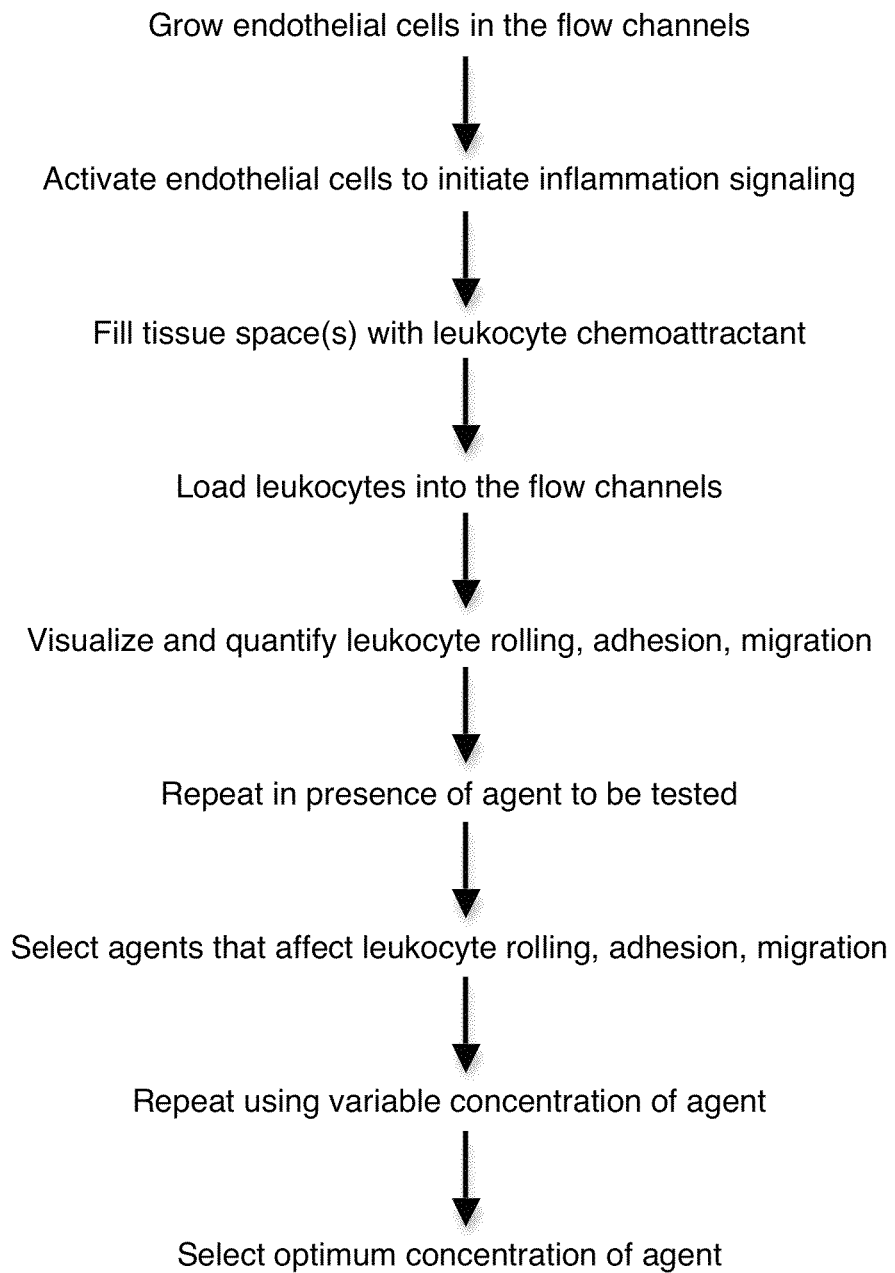
FIG. 11 is a flow chart showing method steps for a leukocyte adhesion cascade assay.
Figure 12:
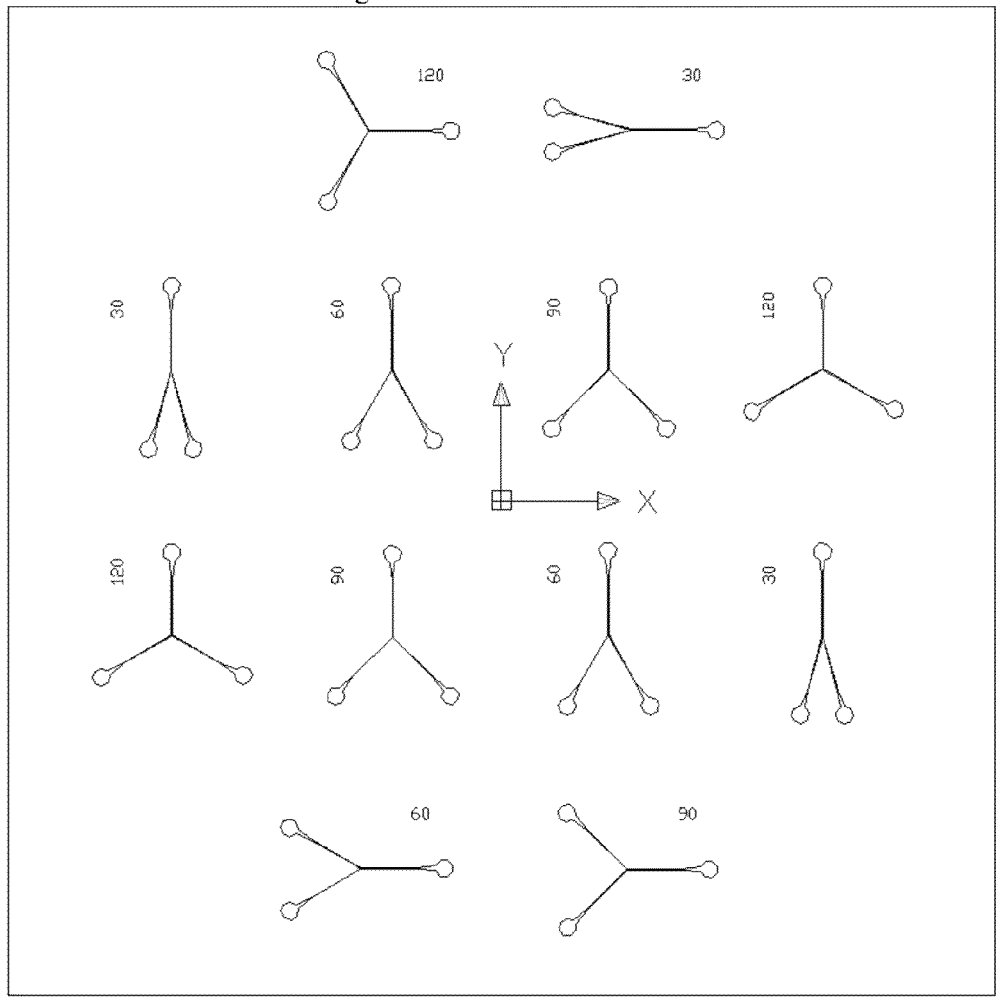
FIG. 12 is a drawing of a microfluidic chip comprising a plurality of symmetric microfluidic bifurcations with 30°, 60°, 90°, and 120° angles configured sequentially for leukocyte adhesion cascade assays.
Figure 13:
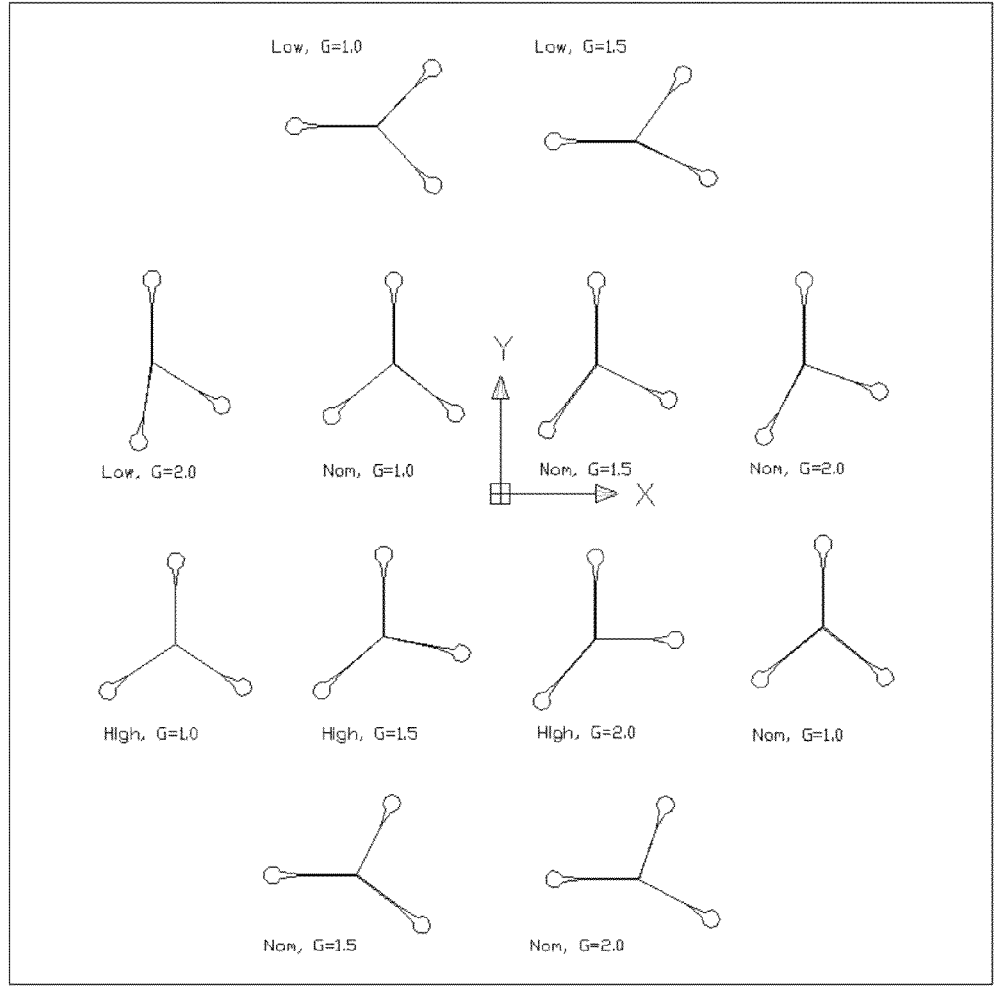
FIG. 13 is a drawing of a microfluidic chip comprising a plurality of asymmetric microfluidic bifurcations with low, nominal, and high contained angles wherein low refers to the smallest contained angle and high refers to the largest contained angle.

The method of the present invention, as shown in FIG. 11, may employ a single idealized bifurcation or junction or, more preferably, the serial or simultaneous use of plurality of junctions and/or bifurcations. It may also use the single straight channel of FIG. 3. FIG. 12 and FIG. 13 illustrate single microfluidic chips, each comprising a plurality of microfluidic bifurcations/junctions arranged for simultaneous use or in a serial fashion, one after another. FIG. 12 shows a microfluidic chip comprising a plurality of symmetric bifurcations with different contained angles (30°, 60°, 90°, and 120°) used sequentially to implement a method of the invention, such as a study a leukocyte adhesion cascade as described herein with IMN devices. FIG. 13 shows a microfluidic chip comprising a plurality of asymmetric bifurcations with Low, Nom, and High contained angles, wherein Low refers to the smallest contained angle, and High refers to the largest contained angle. The degree of angle asymmetry is indicated by G=1, G=1.5, and G=2.0, where increasing G values indicate increasing asymmetry in the bifurcation and the bifurcations are used sequentially to implement a particle and cellular adhesion assay, which can be applied to leukocyte adhesion cascade assays.

Figure 14:
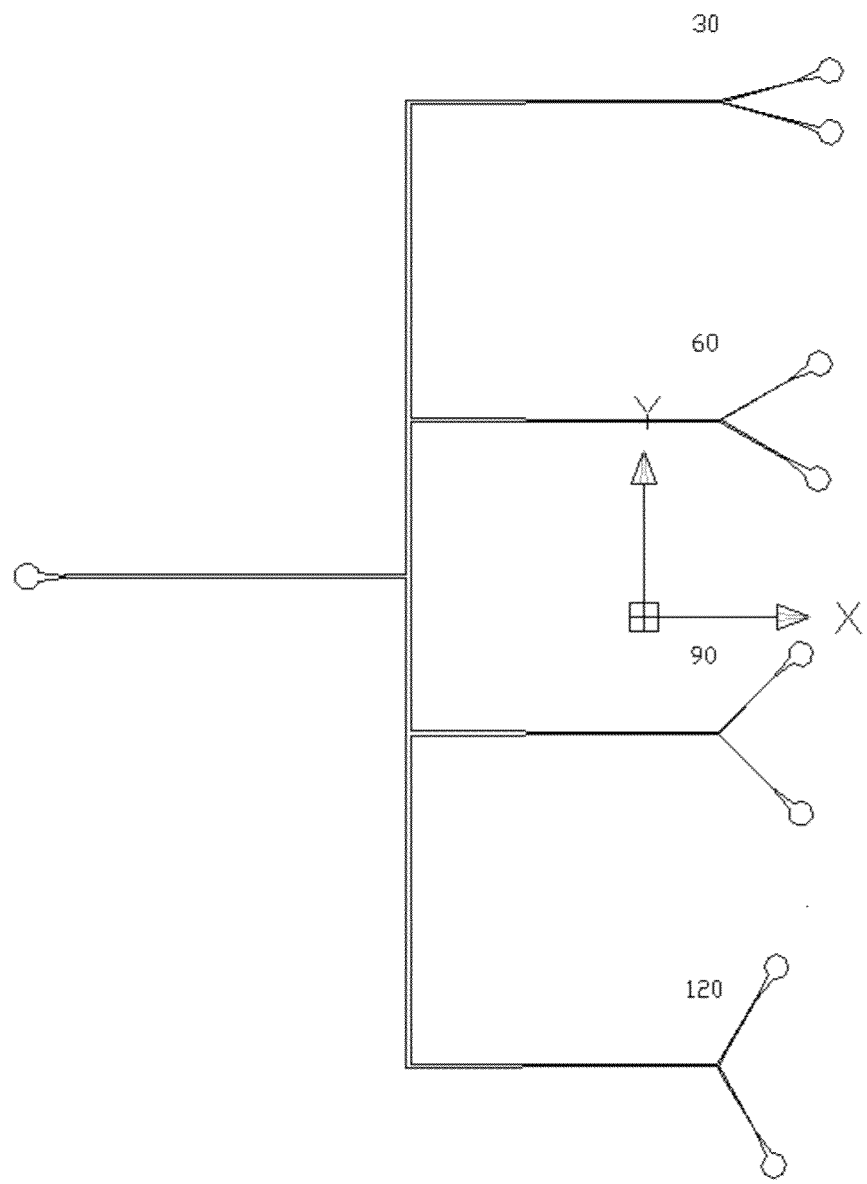
FIG. 14 is a drawing of a single microfluidic chip comprising a plurality of bifurcations arranged in parallel.

The methods of the present invention may also employ a plurality of idealized bifurcations or junctions arranged in parallel or in series. FIG. 14 illustrates a single microfluidic chip comprising a plurality of bifurcations arranged in parallel.

Figure 15:
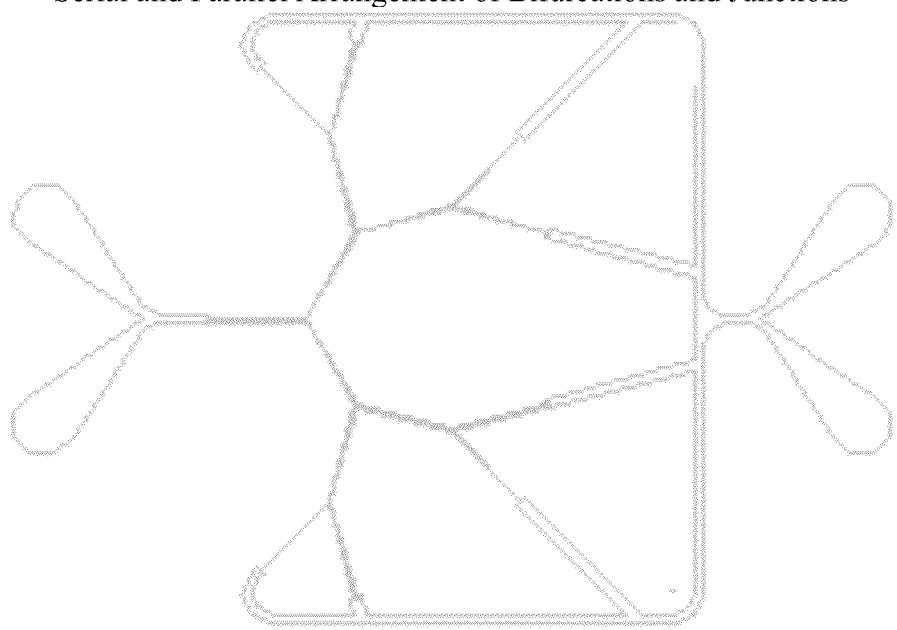
FIG. 15 is a drawing of an idealized microfluidic network comprising a plurality of bifurcations in which no contained angle is repeated and the lengths of the individual branches are maintained constant throughout the network.
Figure 16:
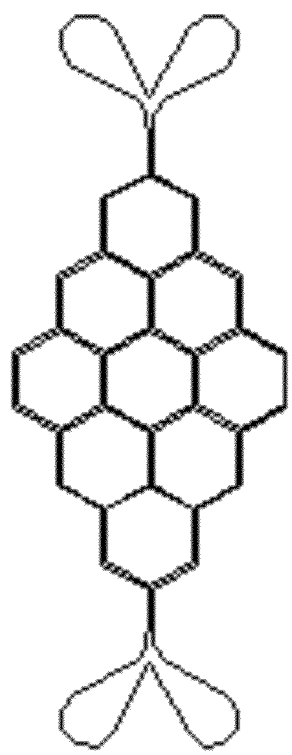
FIG. 16 is a drawing of an idealized microfluidic network comprising a plurality of identical, symmetric bifurcations and junctions.
Figure 17:
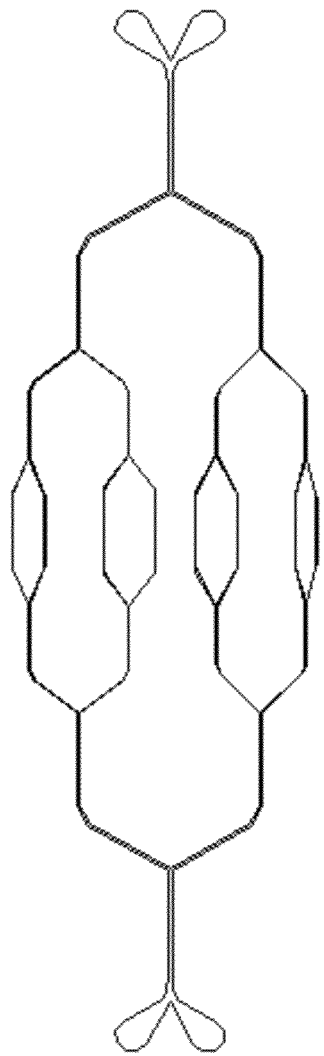
FIG. 17 is a drawing of an idealized microfluidic network comprising a plurality of bifurcations and junctions in which no bifurcation or junction geometry is repeated.

The methods of the present invention may also employ a plurality of idealized bifurcations and junctions arranged to form an idealized microfluidic network. FIG. 15 illustrates a single microfluidic chip comprising a plurality of bifurcations in which no contained angle is repeated and the lengths of the individual branches are maintained constant throughout the network. FIG. 16 illustrates an idealized microfluidic network comprising a plurality of identical, symmetric bifurcations and junctions. FIG. 17 illustrates an idealized microfluidic network comprising a plurality of bifurcations and junctions in which no bifurcation or junction geometry is repeated. The present leukocyte adhesion cascade assay methods may also employ one or a plurality of junctions/bifurcations with more than three channels. Optionally, one or more of the spaces between the channels shown in FIGS. 15-17 can be the tissue spaces as described herein, and the channels can have perforations, holes, pores, or gaps that allow for permeation from the IMN channel into an idealized IMN tissue space.

The IMN can include idealized bifurcations, junctions, and networks of the present invention are preferably made from polydimethylsiloxane (PDMS) using polymeric microfluidic technology but may be made using any one of a variety of techniques commonly used in semiconductor or microfluidic technologies. PDMS offers the advantages of gas permeability beneficial for cell culture, optical transparency, ease of casting, and producing small volume, inexpensive, disposable chips. Very thin (<100 microns) PDMS constructs can be successfully used to for long-term cell culture and cellular assays on microfluidic chips. By bonding the polymer microchannel on to a custom glass bottom laid out in the appropriate form, microfluidic chips may be formed onto standard 24 or 96 well plates, providing for scale-up and high-throughput screening.

The channels forming the bifurcations/junctions may be coated with native or recombinant with proteins, glycoproteins, proteoglycans, or other substrate molecules to assay for associations with particles or to facilitate the growth of cells on the inner surfaces of the channels. Examples of substrate molecules include collagen, gelatin, laminin, and fibronectin. The channels may also be coated with adhesion molecules such as P-selectin, E-selectin, ICAM-1, or other receptors to facilitate adhesion of specific cell types or particles such as liposomes or drug encapsulating or targeting agents. Vascular cells, such as endothelial cells, can also coat the IMN channels.

Microfluidic Chip Fabrication:

Microvascular network structures obtained from in-vivo animal data as for SMN or averaged or idealized microvascular networks (IMN) are patterned onto an optically clear plastic such as PDMS (polydimethylsiloxane) using conventional soft lithography/replica casting techniques and as described in U.S. Ser. No. 11/393,715 to form a SMN. CAD drawings of physiological networks are modified to include gaps in the walls of the vessels. The patterns of these vessels include tissue sections including selected locations ranging from one to the entire tissue space comprising wall sections with gaps with dimensions between 0.2 µm to 30 µm. When fabricated using PDMS, the aspect ratio of these structures should be maintained such that the length (or width) of the structure is greater than twice the channel depth. For 25-50 µm channel depth, this places a minimum requirement on the structure length (and width) of 50-100 µm. The structures are optimally at least 50×50 µm in size. The flow channels may be covered with extracellular matrix components such as fibronectin, collagen, integrins, and other proteins and proteoglycans. Endothelial cells are cultured on the luminal side of the flow channels and cells or tissues (e.g., tumor cells) may be cultured in the tissue space(s). Also, the tissue space(s) can be empty or without cells, and the assay can monitor cell migration into the tissue space(s), which can be useful for leukocyte adhesion cascade assays.

A similar approach is used to fabricate the IMN with gaps with dimensions between 0.2 µm to 30 µm. As before endothelial cells are cultured on the luminal side of the flow channels and tumor cells are cultured in the tissue spaces or the tissue spaces are left empty so that cells (e.g., leukocytes) can migrate into the tissue spaces.

Endothelial cells from any source can be cultured in the vascular channels. Similarly cells (e.g., tumor cells) from any source, whether adherent or suspension or primary or immortalized, can be cultured in the tissue space. For example, the cells can be immortalized cell lines that are commercially available or primary cells taken directly from a subject. As such, the cells can be cancer cells from a tumor or other cancer cells from a specific subject, such that experiments can be conducted on the specific cancer cells from the specific subject. Similarly, the leukocytes can be from any source, such as primary or immortalized or from stem cells, and may be general leukocytes or from a specific subject.

Culture of Endothelial Cells and Cells in Tissue Space:

Sterile phosphate buffer saline is injected into a SMN or an IMN at a flow rate of 10 µl/min for 10 minutes using a syringe pump to prime the device. Extracelluar matrix (e.g. fibronectin, gelatin, and collagen) at a concentration of 50 µg/ml and flow rate of 10 µl/min is introduced into the chamber for 5 minutes. Flow is stopped and fibronectin solution is allowed to incubate for 2 hrs at room temperature to completely saturate the surfaces. Endothelial cells at a concentration of $5 \times 10^3$ to $5 \times 10^7$ cells/ml are introduced into the chamber with media and allowed to incubate for 4 hours. Media is replaced every 24 hours until the cells are confluent (>80%) in the network.

The extracellular tissue spaces are coated with basement membrane matrix such as Matrigel™. (BD Biosciences, Bedford, Mass.). Cells (e.g., tumor cells) are resuspended at a concentration of $5 \times 10^3$ to $5 \times 10^7$ are mixed with Matrigel™ to a final concentration of 0.1 to 1 mg/ml. This mixture is injected into the tissue spaces of the network and allowed to equilibrate in an incubator at 37° C. and 5% $CO_2$ overnight. The microfluidic chip is placed on an automated stage mounted on an inverted microscope equipped with a camera and imaging software.

While the invention is directed primarily toward drugs that modulate the leukocyte adhesion cascade, the methods and apparatus described herein may be altered to assay for drug delivery to other tissues without departing from the spirit of the invention. For example, tissue spaces may contain cells that are not derived from tumors such as non-neoplastic primary cell cultures and cell lines that are transformed to contain recombinant genes. The pore size of porous flow channel walls may also be modified to mimic diffusion across other physiological barriers, including the blood-brain barrier and linings of the small intestine.

Additionally, the devices and methods of the present invention can be combined and applied with the methods and devices of the incorporated references. As such, the methods of the incorporated references, such as particle transport, particle adhesion, blood-brain barrier diffusion, blood-brain barrier delivery, and the like, can be applied with IMN devices and can be used as described herein.

In one embodiment, an optically transparent microfluidic chip can include: one or more idealized flow channels having one or more inlets and one or more outlets and a first cross-sectional dimension; and one or more tissue spaces bordering the one or more idealized flow channels and having a second cross-sectional dimension, wherein a first wall separating a first idealized flow channel from a first tissue space includes a plurality of apertures that fluidly couple the first idealized flow channel with the first tissue space, the plurality of apertures having a third cross-sectional dimension. In one aspect, the third cross-sectional dimension is smaller than the first cross-sectional dimension and the second cross-sectional dimension is larger than the first cross sectional dimension. In one aspect, the first cross-sectional dimension is from 10 microns to 500 microns, the second cross-sectional dimension is from about 100 microns to 1 cm, and the third cross-sectional dimension is from 0.2 microns to 30 microns. In one aspect, the first cross-sectional dimension can be from about 5 microns to about 500 microns, from about 25 microns to about 250 microns, from about 50 microns to about 150 microns, or about 100 microns. In one aspect, the second cross-sectional dimension can be from about 100 microns to about 1 cm, from about 250 microns to about 5 mm, from about 500 microns to about 2.5 mm, or about 1 mm. In one aspect, the third cross-sectional dimension can be from about 0.2 microns to about 30 microns, from about 1 microns to about 10 microns, from about 2 microns to about 7 microns, or about 3 microns, which can be of a size that inhibits leukocyte passage.

Leukocytes often range in size from about 7 microns to about 15 microns (e.g., neutrophils about 10-12 microns, eosinophils about 10-12 microns, basophils about 12-15 microns, small lymphocytes 7-8 microns, large lymphocytes 12-15 microns, and monocytes 7-10 microns). As such, the pores, holes, apertures, or gaps in the walls between fluid channels and tissue spaces can be less than 10 microns to block neutrophils, eosinophils, basophils, and large lymphcoytes, or selectively allow passage of small lymphocytes or monocytes. The pores, holes, apertures, or gaps in the walls between fluid channels and tissue spaces can be less than 15 microns or less than 20 microns or even less than 30 microns to allow passage of neutrophils, eosinophils, basophils, lymphcoytes, or monocytes, or which can selectively block macrophages.

In one aspect, the one or more idealized flow channels form an idealized microvascular network (IMN). In one aspect, the idealized microvascular network includes one or more idealized flow channels interconnected by one or more idealized bends, junctions, or bifurcations. In one aspect, the one or more idealized bends, junctions or bifurcations include one or more acute, right, or obtuse angles. In one aspect, luminal surfaces of the one or more idealized flow channels of the idealized microvascular network are coated with a first cell type (e.g., endothelial) and the one or more tissue spaces are initially devoid of any cells or may include a different second type of cell (e.g., diseased or cancerous). In one aspect, the apertures and/or one or more tissue spaces are filled with a material that is permeable to the second type of cells and/or leukocytes, wherein the material is selected from a gel, a basement matrix, an extracellular matrix, a tissue matrix, a synthetic matrix, a natural matrix, polymer and combinations thereof. In one example, the second type of cell can be leukocytes, where an assay may initially include some leukocytes in the tissue spaces or the tissue spaces may initially be devoid of leukocytes. The leukocytes may migrate into a tissue space through the apertures.

In one embodiment, the apertures are dimensioned smaller than the first or second types of cell so as to be impermeable thereto when the second types of cells are not leukocytes. The apertures are permeable to leukocytes. However, the apertures can still be large enough so as to allow the leukocytes and analytes, such as, to pass from the flow channel through the aperture, and into the tissue spaces.

In one embodiment, the pores can be dimension to block leukocytes. Such small pore sizes can range from about 0.5 microns to about 5 microns, or be about 3 microns. Pores less than 7 microns can block many leukocytes; however, less than 3 microns can be preferred to block most leukocytes.

In one embodiment, the angles of the one or more idealized bends, junctions or bifurcations range from 15° to 135°. In one aspect, a first bifurcation having a first idealized daughter flow channel with a cross-sectional dimension that is greater than a cross-sectional dimension of a second idealized daughter flow channel of the first bifurcation. In one aspect, a first bifurcation having a first idealized daughter flow channel at an angle that is greater than an angle of a second idealized daughter flow channel of the first bifurcation. In one aspect, a first bifurcation having a first idealized daughter flow channel with a cross-sectional dimension that is greater than a cross-sectional dimension of a second idealized daughter flow channel of the first bifurcation and a first idealized daughter flow channel being at an angle that is greater than an angle of a second idealized daughter flow channel.

In one embodiment, the one or more tissue spaces each include a distinct inlet port configured for introducing fluid and/or cells (e.g., leukocytes) therein. In one aspect, a valve is in fluid communication with the distinct inlet port of each tissue space, said valve configured to regulate pressure inside the tissue space. In one aspect, each tissue space includes posts configured to promote growth of 3-dimensional tissues (e.g., diseased tissues or tumors). In one aspect, the one or more tissue spaces each include a distinct outlet port.

In one embodiment, luminal surfaces of the one or more idealized flow channels are coated with a substance selected from the group consisting of a protein, a proteoglycan, a chemical moiety, a biomolecule, and combinations thereof. When the luminal surfaces include endothelial cells, the endothelial cells can include an activating agent such as described herein.

In one embodiment, the one or more flow channels each contain a first type of cell. The one or more tissues spaces can be devoid of cells or include a different second type of cell. In one aspect, the one or more flow channels and/or tissue spaces may contain one or more of endothelial cells, epithelial cells, fibroblasts, bone marrow cells, embryonic cells, hepatocytes, myocytes, neural cells, adipocytes, first type of cancer cell, second type of cancer cell, and/or diseased or normal cells comprised of brain cells, liver cells, heart cells, kidney cells, lung cells, stomach cells, intestine cells, pancreas cells, ovary cells, cervix cells, spleen cells, artery cells, venule cells, capillary cells, connective tissue cells, organ tissue boundary layer cells, connective tissue cells, muscle cells, bone cells, nervous tissue cells, germ cells, stem cells, cultures thereof, 3D tissues thereof, and combinations thereof. The cells can be any type of cell ranging from immortalized cell lines to primary cells to patient-derived cells. In some instance, a tissue culture from a patient can be included. The cell cultures can include a single type of cell or a combination of cells, such as 2, 3, or 4 different types in a co-culture. In some natural tissues, multiple cells may be present, and such tissues can be simulated with a similar cell type combination. For example, the flow channels and/or tissue spaces can include cells or cell cultures that simulate healthy or diseased liver, kidney, heart, lung, brain, stomach, intestine, blood brain barrier, vascular networks, or other organs. As such, the flow channels and/or tissue spaces can have unique cell cultures that are indicative of the different cell types or tissue types of an organ, where the cell culture in the flow channels can be different from the cell culture in the tissue space. Often, the tissue space does not initially include cells, but the leukocytes migrate into the tissue spaces during a leukocyte adhesion cascade assay.

The cells (e.g., endothelial) can grow only on the bottom, or can grow to confluence on the sides and optionally the top walls of the flow paths and tissue spaces. As such, the cells can grow over the pores of the walls that separate the flow paths from the tissue spaces. Preferably, the cells grow completely around the flow paths and tissue spaces to form a cellular lumen or three-dimensional tissues. Tissue culture scaffold materials can be located in any or all of the tissue spaces as desired. The cells (e.g., endothelial) can grow over the pores on the flow path side but allow analytes or metabolites or other fluid to pass through the pores to an adjacent tissue space. The cells can start growing at the bottom of a flow path or tissue space first, but eventually they fill up the porous side walls and the top walls and all around the flow paths or tissue spaces.

In one embodiment, the one or more tissue spaces are defined by at least two of the idealized flow channels having walls that each include the plurality of apertures that fluidly couple the at least two straight flow channels with the first tissue space. In one aspect, the at least two idealized flow channels each include idealized flow channels connected at bends for form at least two distinct flow channel lumen that define the first tissue space. In one aspect, each wall separating one or more idealized flow channels from the first tissue space include the plurality of apertures that fluidly couple the at least two straight flow channels with the first tissue space.

In one embodiment, a method is provided for assaying a drug and/or drug delivery vehicle with the IMN. The method includes: providing the optically transparent microfluidic chip of having the one or more idealized flow channels and one or more tissue spaces separated by walls having the plurality of apertures; introducing leukocytes into the one or more idealized flow channels and/or one or more tissue spaces; introducing a liquid containing a drug delivery vehicle and/or a drug into a first inlet of the one or more idealized flow channels; causing the liquid containing the drug delivery vehicle and/or the drug to move through the one or more idealized flow channels, through the plurality of apertures, and/or into the one or more tissue spaces; and quantifying the amount of the drug delivery vehicle and/or a drug and/or leukocytes reaching the tissue space.

In one embodiment, the method can include providing the optically transparent microfluidic chip that includes luminal surfaces of the one or more idealized flow channels of the idealized microvascular network are coated with a first cell type and the one or more tissue spaces are devoid of cells or include a different second type of cell; introducing leukocytes into the one or more idealized flow channels and/or one or more tissue spaces; introducing a liquid containing a drug delivery vehicle and/or a drug into a first inlet of the one or more idealized flow channels; causing the liquid containing the drug delivery vehicle and/or the drug to move through the one or more idealized flow channels, through the plurality of apertures, and/or into the one or more tissue spaces; and quantifying the amount of the drug delivery vehicle and/or a drug interacting with the leukocytes.

In one embodiment, the method can include: providing the optically transparent microfluidic chip with one or more idealized flow channels and one or more tissue spaces devoid of leukocytes; introducing leukocytes into the one or more idealized flow channels and/or one or more tissue spaces; introducing a liquid containing a drug delivery vehicle and/or a drug into a first inlet of the one or more idealized flow channels; causing the liquid containing the drug delivery vehicle and/or the drug to move through the one or more idealized flow channels, through the plurality of apertures, and/or into the one or more tissue spaces; and quantifying the amount of the drug delivery vehicle and/or a drug interacting with the leukocytes.

The device can be used to test the effect of any substance on the leukocytes adhesion cascade, or test ability of the substance to reach the leukocytes or other cells in discrete locations in the flow channels or reach the cells in the tissue spaces. The substance can be a biologically active agent that can be any agent that is administered for a function, such as a biological function to improve or otherwise modulate a biological process, such as a biological pathway. However, the agent can be active, such as to emit light, without being biologically active. As such, the biologically active agent can be a traditional pharmaceutical or nutraceutical, and it can be any type of substance for testing or diagnostics. The biologically active agent can be any agent that is administered to a subject in order to elicit a biological response that arises from the biological activity of the agent. The biological response obtained can be a measurable biological response or provide some change that can be analyzed and determined, such as by testing to determine an amount of the biologically active agent to be administered. The biologically active agent can be a toxin or poison or other deleterious substance. Examples can include the biologically active agent being a mineral, vitamin, pharmaceutical, nutraceutical, small molecule, macromolecule, organic molecule, polypeptide, protein, nucleic acid, polynucleotide, derivatives thereof, and combinations thereof. The biologically active agent can be for a human or animal subject. Human and veterinary medicines can be evaluated and improved with the present invention. The substance can be an environmental substance that is natural or manmade and found in the environment. The substance can be a particle. The substance can be a foreign cell not found in an organ, such as a cancer cell, bacteria, yeast, or the like, and even a virus. The test substance can be a particle, such as a micro particle or microsphere.

The test substance to modulate the leukocyte adhesion cascade can even be a substance commonly used in a pharmaceutical product or combination thereof. The test substance can include the following: a film-forming agent; a filler; a plasticizer; a taste-masking agent; a coloring agent; a solubilizing agent; an effervescent agent; an antioxidant; an absorption enhancer; a disintegrating agent; a pH modifying or buffer agent; a surfactant; a complexing agent; a bioadhesive agent; a sheet adhesive; an identifying agent; an anti-counterfeiting agent; a tracking agent; transporter inhibitor agent; transporter inducer agent; emulsifying agent, self-emulsifying system agents; crystallization inhibitor; crystallization promoter; supersaturation promoting agent; antimicrobial preservative; catalyst; chelating agent; particles; organoleptic agent; flavoring agent; scent agent; identifying device; and/or anti-counterfeiting device.

In one embodiment, leukocytes or other cells can be analyzed in any of the flow paths or tissue spaces. However, in some assays, only the leukocytes or other cells in the tissue spaces will be assayed. For example, visual analysis, such as with a microscope can be used for analysis of the leukocytes or other cells. In another example, the leukocytes or other cells can be identified using optical or electrical methods. For example, cell staining markers specific for cell types can be used. In addition, electrical signals based detection can allow detection of morphology changes (cell differentiation) and different types of cells.

The device may be connected to a flow or pressure regulating system that can regulate the pressure across the flow paths and tissue spaces or within each distinct tissue space. Pumps and valves can be used to regulate the pressure. As such, operation of the device can include regulating the pressures inside each of the flow paths and tissue spaces. For example, a tissue such as liver or the kidney may be leaky, pressure control can be used to simulate such leakiness of the tissue. Also, some tissue like the brain can have very high pressures, which can be simulated with controlling the pumps and valves. The system can regulate the pressure in each of these flow paths and tissue spaces as desired to mimic normal vs. diseased conditions.

General Leukocyte Adhesion Method

One exemplary set of method steps for a LAC assay according to the present invention is outlined in FIG. 11. The flow channels are coated with a layer of cells, preferably a confluent layer of cells. The cells are preferably primary endothelial cells or a cultured endothelial cell line, or endothelial cells from any source such as stem cells. The flow channels may first be coated with a substance to facilitate cell adhesion, such as extracellular matrix proteins or proteoglycans or other substances described herein. In most cases, the layer of endothelial cells is activated before leukocytes are introduced into the device. The cytokine, TNF-α is commonly used for activation of endothelial cells but any substance capable of activating the cells may be used. Pores or pores and extravascular tissue spaces may be filled with a gel such as Matrigel® to provide a medium through which leukocytes can migrate. In other conditions, pores may be filled with just cell media, buffer solutions and combinations. For stimulating leukocyte migration, a source for a leukocyte-attracting cytokine or other leukocyte chemo-attractant may be introduced into at least one extravascular space (e.g., tissue space). A suspension of leukocytes is introduced into the device and allowed to circulate or allowed to incubate, depending on the purpose of the assay. Leukocytes may be recirculated through the device at a single or multiple flow rates to assess the effect of shear forces on leukocyte rolling, adhesion, and/or migration modulation. The locations of leukocytes and numbers of leukocytes in different locations within the device over time are captured by digital camera or other optical means and stored in a computer. The degree of leukocyte rolling, adhesion, and/or migration modulation is measured by comparing the numbers of leukocytes located at various positions in the device over time, providing end point and kinetic values for leukocyte cascade activation. Leukocytes may be introduced into the chip at desired time points following activation to reproduce the complete adhesion cascade. One or more chemo-attractants may be introduced into one or more extravascular tissue spaces to stimulate migration. Rolling, adhesion and migration of leukocytes into the one or more extravascular tissue spaces may be captured in real-time by scanning the entire network. Drug screening may be performed, for example, by the injection of potential cascade inhibitors to analyze the effect on adhesion and migration.

EXAMPLE 1

Leukocyte Rolling and Adhesion on Activated Endothelium

A microfluidic chip comprising a SMN is degassed by vacuum for 5 minutes and placed on an automated stage that is mounted on a microscope equipped with a camera. The entire chamber is housed in an incubation chamber configured to maintain temperature, $CO_2$ concentration, and humidity.

Sterile phosphate buffered saline is injected into an inlet port at a flow rate of 10 µl/min for 10 minutes to prime the chip. Following priming, fibronectin (50 µg/ml) is introduced into the inlet port for 5 minutes at a flow rate of 10 µl/min. The fibronectin solution is allowed to incubate in the device for 2 hrs at room temperature to completely saturate all the surfaces. Primary endothelial cells at a concentration of $5 \times 10^6$ cells/ml in media are introduced into the inlet port and incubated at 37° C. and 5% $CO_2$. Media is perfused continuously until the cells are confluent in the device. The confluent endothelial cells are activated by perfusion with TNF-α at a concentration of 10 U/ml for 4 hr or 24 hr. In other method, endothelial cells at a concentration of $5 \times 10^7$ can be introduced into the device so that the cells are confluent within 24 hours.

Leukocytes at a concentration of approximately $10^5$-$10^7$ cells/ml are perfused into the device via inlet at a flow rate corresponding to a shear rate of 500 $sec^{-1}$ for 30 minutes using a peristaltic pump for looping or via a syringe pump for single pass. Software is used to automatically control the stage, camera and the timing for image acquisition and scanning of the entire device. Rolling and adhered leukocytes are imaged and quantified using image analysis software.

Complex flow in the device may be characterized experimentally or using computational fluid dynamics (CFD) simulations in advance of the assay and stored in a database. The experiment may be repeated using flow rates corresponding to different shear rates or the device can be designed to incorporate regions providing different shear rates at the same flow rate at the inlet or inlets to allow data collection producing a curve of number of rolling cells vs. shear rate or number of adhered cells vs. shear rate.

The experiment may be repeated in the presence of one or more agents such as drug candidates to identify one or more drugs, alone or in combination, that affect, either positively or negatively, leukocyte rolling and/or adhesion based upon the relative numbers of leukocytes counted as rolling or adherent.

EXAMPLE 2

Leukocyte Rolling, Adhesion, and/or Migration on Activated Endothelium

The microfluidic chip is prepared and flow channels coated by a confluent layer of endothelial cells as in Example 1. The extravascular tissue spaces of the device are filled with a solution containing a chemo-attractant such as N-Formyl-L-methionyl-L-leucyl-L-phenylalanine (fMLP) diluted in cell media to a concentration of 10 nM-10 mM. Following the injection of fMLP, leukocytes are introduced into the inlet port of the device and allowed to adhere to the endothelial cells using the protocol in Example 1. Following 30 minutes of the cell flow, the flow is switched to a cell free media to wash off circulating unbound leukocytes. Cell media is maintained for 24 hr by circulating perfusion at a selected shear rate of 120 $sec^{-1}$. The device is repeatedly scanned and imaged, as in Example 1, every 30 minutes for 24 hr. Any cells that leave the vessel area (lumen of the network) and migrate into the tissue area are digitally photographed and counted. At the end of the respective time point, the individual images are merged together to create a time-lapse composite image to quantify the number of cells that have migrated. A plot of cells migrated vs. the local shear rate may also generated using data from successive or parallel variable shear rate conditions. In addition, the geometric features of the adhesion sites can be recorded to allow for distinction between (a) shear only, or (b) shear and geometry based adhesion/migration. Fluorescent live cell dyes may be used to supplement phase contrast microscopy to aid in tracking migrated cells. The flow values, such as shear rate, can be modified such as described herein.

The experiments described in Example 2 may also be performed using a microfluidic chip in which the pores in the walls of the flow channel separating the vascular lumen from the extravascular tissue space are filled with a gel, such as Matrigel®. In this case, Matrigel® is placed into pores desired locations of the device.

Matrigel® is mixed to a final concentration of 1 mg/ml in serum free cold media. The Matrigel® solution is injected into the prescribed tissue areas of the device. A small amount of vacuum is applied in the channels to aid in movement of the Matrigel® solution into the gaps. Following vacuum treatment, the Matrigel® solution is pipetted out from the tissue area leaving the Matrigel® in the gaps intact. A confluent layer of endothelial cells is subjected to the leukocytes migration assay in the same manner as before in the presence and absence of fMLP. The migration capability of leukocytes can be compared to obtain a migration vs. shear rate plot.

The experiments described in Example 2 may also be performed in a static mode in which leukocytes are injected into the device and allowed to incubate for 30 minutes. Following incubation, the unbound cells are washed out of the device using cell free media. The devices are then be scanned every 30 minutes for 24 hours to take time-lapse images. At the end of 24 hours, the images are visualized to identify migrated cells. The migration data in absence of fluidic conditions may be compared with that of fluidic conditions to extract the difference between the two procedures. Transient rate of migration of the cells can also be quantified by measuring the distance traversed in the time period.

Experiments may be performed sequentially or simultaneously and may be performed using the same microfluidic chip containing a plurality of devices and/or different microfluidic chips separately or together. Incubation times, flow rates, and reagent concentrations are provided as non-limiting examples and those skilled in the art will appreciate that the precise times, rates, and concentrations used may be and should be varied according to the specific assay and microfluidic chip designs.

EXAMPLE 3

Identifying Agents that Affect Leukocyte Rolling, Adhesion and Migration on Activated Endothelium One or more agents that modulate leukocyte rolling, adhesion, and/or migration may be identified by repeating the experiment in the presence of and/or after pretreatment with one or more candidate agents as in Example 2 in addition to counting migrated cells. Two classes of adhesion molecules involved in the adhesion cascade are selectins and integrins. Antibody-based inhibition of E-selectin reduces leukocyte rolling and antibody-based inhibition of ICAM-1 reduces leukocyte adhesion. Wortmannin, a fungal metabolite has been found to inhibit fMLP dependent migration.

Inhibition of Rolling: Monoclonal antibodies to E-Selectin are injected into the device and allowed to incubate on the endothelial cells for 30 minutes at 37° C. in 5% CO2. Cell free media is flown to wash off unbound antibodies followed by injection of leukocytes into the device. fMLP is injected into the tissue section and rolling, adhesion and migration of the cells are quantified.

Inhibition of Adhesion: Monoclonal antibodies to ICAM-1 are injected and allowed to incubate for 30 minutes followed by a wash to remove unbound antibodies. fMLP is injected as before and rolling, adhesion and migration of the cells are quantified.

Inhibition of Rolling and Adhesion: In this step, both E-selectin and ICAM-1 monoclonal antibodies are incubated together for 30 minutes followed by a wash. Leukocytes are introduced into the device and migration of the cells is quantified in presence of fMLP.

Inhibition of Migration Only: Wortmanin, the fungal metabolite which blocks fMLP dependent migration is mixed with leukocytes at a concentration of 50 nM for 30 minutes at 37° C. Following mixing, leukocytes are injected into the activated device in the presence of fMLP in the tissue sections. Rolling, adhesion and migration of the cells are quantified.

Inhibition of Rolling, Adhesion and Migration: In this step, monoclonal antibodies to E-selectin and ICAM-1 are incubated for 30 minutes. Leukocytes mixed with Wortmanin are injected into the device. Rolling, adhesion and migration of the cells are quantified again in presence of fMLP.

The agent need not be a protein or macromolecule, but may be any small molecule or macromolecule drug candidate with or without a corresponding drug delivery vehicle.

In one example, the leukocytes can be studied in an assay where the tissue spaces are empty or do not contain cell. In another example, the leukocytes can be studied in an assay where the tissue space includes some cells or tissues, where the cells or tissues do not include cancerous cells or tumors. In another example, the leukocytes can be studied in an assay where the tissue space includes some cells or tissues that may be considered to be diseased cells, where the diseased cells or tissues do not include cancerous cells or tumors. In another example, the leukocytes can be studied in an assay where the tissue space includes some cancerous cells or tumors. In another example, the leukocytes can be studied in an assay where the tissue space includes a foreign material, bacteria, virus, or fungi, or other infectious material.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a range having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited herein are incorporated herein by specific reference in their entirety.

This patent document incorporates by specific reference in their entirety the following patents and patent applications: U.S. Ser. No. 11/393,715 now U.S. Pat. No. 7,725,267 (C1478.10001US01); U.S. Ser. No. 12/648,296 now U.S. 2010/0099136 (C1478.10001US02); U.S. Ser. No. 12/428, 134 now U.S. Pat. No. 8,175,814 (C1478.10001US03); U.S. Ser. No. 12/612,573 now U.S. 2010/0112550 (C1478.10001US04); U.S. Ser. No. 12/726,140 now U.S. 2011/0104658 (C1478.10013US01); U.S. Ser. No. 13/332, 400 (C1478.10001US05); Ser. No. 12/399,606 now U.S. 2010/0227312 (C1478.10009US01); 61/730,357 (C1478.10017US01); and Ser. No. 13/715,350 (C1478.10001US06).

The invention claimed is:

1. A method for identifying one or more agents that modulate leukocyte rolling, adhesion, and/or migration, the method comprising:
   providing an optically transparent microfluidic chip comprising:
      one or more idealized flow channels having one or more inlets and one or more outlets and a first cross-sectional dimension; and
      one or more tissue spaces bordering and fluidly coupled with the one or more idealized flow channels and having a second cross-sectional dimension, wherein the one or more idealized flow channels surround the one or more tissue spaces,
   wherein a first wall separating a first idealized flow channel from a first tissue space includes a plurality of apertures that fluidly couple the first idealized flow channel with the first tissue space, the plurality of apertures having a third cross-sectional dimension;
   flowing a suspension of leukocytes through the one or more idealized flow channels;
   flowing a solution containing one or more agents through the one or more idealized flow channels before, during, or after flowing the suspension of leukocytes;
   locating and counting leukocytes in the microfluidic chip; and
   based upon the locations and numbers of leukocytes, determining whether the one or more agents modulate leukocyte rolling, adhesion, and/or migration.

2. The method of claim 1, wherein the third cross-sectional dimension is smaller than the first cross-sectional dimension and the second cross-sectional dimension is larger than the first cross sectional dimension.

3. The method of claim 2, wherein the first cross-sectional dimension is from 10 microns to 500 microns, the second cross-sectional dimension is from about 100 microns to 1 cm, and the third cross-sectional dimension is from 0.2 micron to 30 microns.

4. The method of claim 3, wherein the one or more idealized flow channels form an idealized microvascular network having a plurality of idealized flow channels.

5. The method of claim 4, wherein the idealized microvascular network includes one or more idealized flow channels interconnected by one or more idealized bends, junctions, or bifurcations.

6. The method of claim 5, wherein the one or more idealized bends, junctions or bifurcations include one or more acute, right, or obtuse angles.

7. The method of claim 6, wherein luminal surfaces of the one or more idealized flow channels of the idealized microvascular network are coated with a first cell type and the one or more tissue spaces are either devoid of cells or include a different second type of cell.

8. The method of claim 7, wherein the apertures and/or one or more tissue spaces are filled with a material that is permeable to the leukocytes, wherein the material is selected from a gel, a basement matrix, an extracellular matrix, a tissue matrix, a synthetic matrix, a natural matrix, polymer and combinations thereof.

9. The method of claim 6, wherein the angles of the one or more idealized bends, junctions, or bifurcations range from 15° to 135°.

10. The method of claim 9, comprising a first bifurcation having a first idealized daughter flow channel with a cross-sectional dimension that is greater than a cross-sectional dimension of a second idealized daughter flow channel of the first bifurcation.

11. The method of claim 9, comprising a first bifurcation having a first idealized daughter flow channel at an angle that is greater than an angle of a second idealized daughter flow channel of the first bifurcation.

12. The method of claim 9, comprising a first bifurcation having a first idealized daughter flow channel with a cross-sectional dimension that is greater than a cross-sectional dimension of a second idealized daughter flow channel of the first bifurcation and a first idealized daughter flow channel being at an angle that is greater than an angle of a second idealized daughter flow channel.

13. The method of claim 6, wherein the one or more tissue spaces are defined by at least two of the idealized flow channels having walls that each include the plurality of apertures that fluidly couple the at least two straight flow channels with the first tissue space.

14. The method of claim 13, wherein the at least two idealized flow channels each include idealized flow channels connected at idealized bends, junctions, or bifurcations to form at least two distinct flow channel lumen that define the first tissue space.

15. The method of claim 14, wherein each wall separating one or more idealized flow channels from the first tissue space include the plurality of apertures that fluidly couple the at least two straight flow channels with the first tissue space.

16. The method of claim 7, wherein the first type of cell includes endothelial cells, and the second type of cell includes endothelial cells different from the first type of endothelial cells, epithelial cells, fibroblasts, bone marrow cells, embryonic cells, hepatocytes, myocytes, neural cells, adipocytes, brain cells, liver cells, heart cells, kidney cells, lung cells, stomach cells, intestine cells, pancreas cells, ovary cells, cervix cells, spleen cells, artery cells, venule cells, capillary cells, connective tissue cells, organ tissue boundary layer cells, connective tissue cells, muscle cells, bone cells, nervous tissue cells, germ cells, stem cells, leukocytes, erythrocytes, platelets, tumors cultures thereof, 3D tissues thereof, and combinations thereof.

17. The method of claim 1, wherein locating and counting leukocytes is performed by optical means.

18. The method of claim 17, wherein said optical means comprises a camera in communication with an automated stage upon which the microfluidic chip is mounted.

19. The method of claim 1, where the one or more agents that modulate leukocyte rolling, adhesion or migration is selected from the group consisting of cells, liposomes, lipisomes, lipoproteins, microencapsulated drugs, particulate drug carriers, nanoparticles, microparticles, polymer beads, naturally occurring proteins, synthetic proteins, natural compounds, synthetic compounds, and combinations thereof.

20. The method of claim 1, wherein the step of flowing the one or more agents is performed using a flow scheme selected from a single pass, a multiple pass, a recirculating circulation loop, and combinations thereof.

21. The method of claim 1, further comprising measuring a property of the one or more agents, said property selected from the group consisting of real time circulation, stability, half-life, aggregation, degradation, and combinations thereof.

22. The method of claim 1, wherein the step of flowing the solution containing the agent is performed using varying fluidic shear rate values of between 1 $sec^{-1}$ and 5000 $sec^{-1}$.

23. The method of claim 1, wherein the solution containing the one or more agents comprises a component selected from the group consisting of serum proteins, whole blood, apheresed blood, eukaryotic cells, bacteria, erythrocytes, platelets, viruses, and combinations thereof.

24. The method of claim 1, wherein the one or more tissue spaces contain one or more substances selected from the group consisting of an extracellular matrix, a basement membrane, a synthetic matrix, natural occurring matrix, a cytokine, a cell that secrete a cytokine, a gel, a cell culture, a source of a leukocyte chemo-attractant, and combinations thereof.

25. The method of claim 1, and further comprising determining a correlation between flow rate and shear rate for the microfluidic chip and using the determined correlation to set a flow rate for the step of flowing the suspension of leukocytes.

26. A method for identifying one or more agents that modulate leukocyte rolling, adhesion, and/or migration, the method comprising:
providing an optically transparent microfluidic chip comprising:
one or more idealized flow channels having one or more inlets and one or more outlets and a first cross-sectional dimension; and
one or more tissue spaces bordering and fluidly coupled with the one or more idealized flow channels and having a second cross-sectional dimension, wherein the one or more idealized flow channels define a perimeter of the one or more tissue spaces,
wherein a first wall separating a first idealized flow channel from a first tissue space includes a plurality of apertures that fluidly couple the first idealized flow channel with the first tissue space, the plurality of apertures having a third cross-sectional dimension;
flowing a suspension of leukocytes through the one or more idealized flow channels;
flowing a solution containing one or more agents through the one or more idealized flow channels before, during, or after flowing the suspension of leukocytes;
locating and counting leukocytes in the microfluidic chip; and
based upon the locations and numbers of leukocytes, determining whether the one or more agents modulate leukocyte rolling, adhesion, and/or migration.

27. A method for identifying one or more agents that modulate leukocyte rolling, adhesion, and/or migration, the method comprising:
providing an optically transparent microfluidic chip comprising:
one or more idealized flow channels having one or more inlets and one or more outlets and a first cross-sectional dimension; and
one or more tissue spaces bordering and fluidly coupled with the one or more idealized flow channels and having a second cross-sectional dimension, wherein the one or more idealized flow channels and the one or more tissue spaces are planar,
wherein a first wall separating a first idealized flow channel from a first tissue space includes a plurality of apertures that fluidly couple the first idealized flow channel with the first tissue space, the plurality of apertures having a third cross-sectional dimension;
flowing a suspension of leukocytes through the one or more idealized flow channels;
flowing a solution containing one or more agents through the one or more idealized flow channels before, during, or after flowing the suspension of leukocytes;
locating and counting leukocytes in the microfluidic chip; and
based upon the locations and numbers of leukocytes, determining whether the one or more agents modulate leukocyte rolling, adhesion, and/or migration.

28. A method for identifying one or more agents that modulate leukocyte rolling, adhesion, and/or migration, the method comprising:
providing an optically transparent microfluidic chip comprising:
one or more idealized flow channels having one or more inlets and one or more outlets and a first cross-sectional dimension; and
one or more tissue spaces bordering and fluidly coupled with the one or more idealized flow channels and having a second cross-sectional dimension, wherein luminal surfaces of the one or more idealized flow channels are coated with a first cell type and the one or more tissue spaces are either devoid of cells or include a different second type of cell, wherein a first wall separating a first idealized flow channel from a first tissue space includes a plurality of apertures that fluidly couple the first idealized flow channel with the first tissue space, the plurality of apertures having a third cross-sectional dimension;

flowing a suspension of leukocytes through the one or more idealized flow channels;

flowing a solution containing one or more agents through the one or more idealized flow channels before, during, or after flowing the suspension of leukocytes;

locating and counting leukocytes in the microfluidic chip; and based upon the locations and numbers of leukocytes, determining whether the one or more agents modulate leukocyte rolling, adhesion, and/or migration.

* * * * *